United States Patent
Yoshida et al.

(10) Patent No.: US 10,505,123 B2
(45) Date of Patent: Dec. 10, 2019

(54) COMPOUND AND ORGANIC ELECTROLUMINESCENT DEVICE USING SAME

(71) Applicant: IDEMITSU KOSAN CO., LTD., Tokyo (JP)

(72) Inventors: Kei Yoshida, Sodegaura (JP); Toshihiro Iwakuma, Sodegaura (JP); Ryohei Hashimoto, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 104 days.

(21) Appl. No.: 14/903,746

(22) PCT Filed: Jul. 7, 2014

(86) PCT No.: PCT/JP2014/003589
§ 371 (c)(1),
(2) Date: Jan. 8, 2016

(87) PCT Pub. No.: WO2015/004896
PCT Pub. Date: Jan. 15, 2015

(65) Prior Publication Data
US 2016/0163996 A1    Jun. 9, 2016

(30) Foreign Application Priority Data

Jul. 11, 2013    (JP) ................... 2013-145586

(51) Int. Cl.
*H01L 51/50* (2006.01)
*H01L 51/00* (2006.01)
(Continued)

(52) U.S. Cl.
CPC ........ *H01L 51/0071* (2013.01); *C07D 519/00* (2013.01); *C09K 11/06* (2013.01);
(Continued)

(58) Field of Classification Search
CPC ............. H01L 51/5016; H01L 51/5072; H01L 51/0058; H01L 51/0059; H01L 51/006;
(Continued)

(56) References Cited

U.S. PATENT DOCUMENTS

2004/0062949 A1    4/2004 Pfeiffer et al.
2009/0302742 A1    12/2009 Komori et al.
(Continued)

FOREIGN PATENT DOCUMENTS

JP              3695714 B2    9/2005
KR    10-2011-0066766 A    6/2011
(Continued)

OTHER PUBLICATIONS

Du et al., Inden[2,1-c]fluorene-based blue fluorescent oligomers and polymers: Synthesis, structure, photophysical and electroluminscent properties, 2013, Polymer, 54, 2935-2944 (Year: 2013).*
(Continued)

*Primary Examiner* — Gregory D Clark
(74) *Attorney, Agent, or Firm* — Foley & Lardner LLP

(57) ABSTRACT

A compound that includes a structure including two or more structures represented by the following formula (1) in the same molecule and in which at least two of the structures represented by the formula (1) are directly bonded to each other by a single bond.

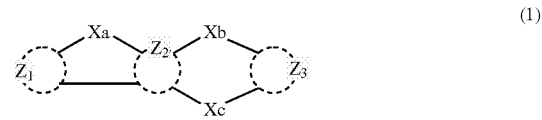

19 Claims, 1 Drawing Sheet

(51) Int. Cl.
*C07D 519/00* (2006.01)
*C09K 11/06* (2006.01)

(52) U.S. Cl.
CPC .. *H01L 51/0073* (2013.01); *C09K 2211/1029* (2013.01); *C09K 2211/1088* (2013.01); *C09K 2211/1092* (2013.01); *H01L 51/006* (2013.01); *H01L 51/0058* (2013.01); *H01L 51/0059* (2013.01); *H01L 51/0067* (2013.01); *H01L 51/0072* (2013.01); *H01L 51/0085* (2013.01); *H01L 51/5016* (2013.01); *H01L 51/5056* (2013.01); *H01L 51/5072* (2013.01)

(58) Field of Classification Search
CPC ............ H01L 51/0067; H01L 51/0071; H01L 51/0072; H01L 51/0073; H01L 51/0085; C07D 519/00; C09K 2211/1029; C09K 2211/1088; C09K 2211/1092
See application file for complete search history.

(56) References Cited

U.S. PATENT DOCUMENTS

| | | |
|---|---|---|
| 2009/0302743 A1 | 12/2009 | Komori et al. |
| 2010/0012931 A1* | 1/2010 | Kato .................... C07D 209/86 257/40 |
| 2010/0314644 A1 | 12/2010 | Nishimura et al. |
| 2012/0068170 A1 | 3/2012 | Pflumm et al. |
| 2013/0168663 A1 | 7/2013 | Gerhard et al. |
| 2013/0299743 A1* | 11/2013 | Pan .................... C08G 61/12 252/301.35 |
| 2014/0014940 A1 | 1/2014 | Pflumm et al. |
| 2014/0275530 A1* | 9/2014 | Jatsch .................. C07D 495/04 544/180 |

FOREIGN PATENT DOCUMENTS

| | | |
|---|---|---|
| WO | WO-2007/063754 A1 | 6/2007 |
| WO | WO-2009/148016 A1 | 12/2009 |
| WO | WO-2009/148062 A1 | 12/2009 |
| WO | WO-2010/136109 A1 | 12/2010 |
| WO | WO-2010/143434 A1 | 12/2010 |
| WO | WO-2011/025282 A2 | 3/2011 |
| WO | WO-2011/149284 A2 | 12/2011 |
| WO | WO-2012/013271 A1 | 2/2012 |
| WO | WO 2012-067425 A1 * | 5/2012 ............ C09K 11/06 |
| WO | WO-2012/136295 A1 | 10/2012 |
| WO | WO-2013/056776 A1 | 4/2013 |
| WO | WO-2013/157886 A1 | 10/2013 |
| WO | WO-2013/179645 A1 | 12/2013 |
| WO | WO-2014/106524 A1 | 7/2014 |

OTHER PUBLICATIONS

International Search Report and Written Opinion issued in corresponding application No. PCT/JP2014/003589 dated Sep. 30, 2014.
Translation of the Written Opinion of the International Searching Authority issued in corresponding application No. PCT/JP2014/003589 dated Jan. 21, 2016.

* cited by examiner

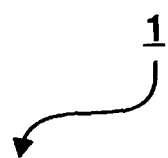
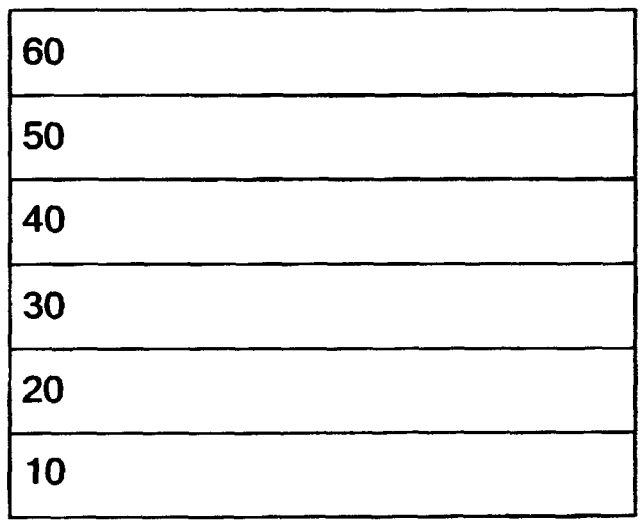

COMPOUND AND ORGANIC ELECTROLUMINESCENT DEVICE USING SAME

The invention relates to a compound and an organic electroluminescence device using the same.

BACKGROUND ART

An organic electroluminescence (EL) device is classified into a fluorescent organic EL device and a phosphorescent organic EL device, and a device design optimum for the emission mechanism of each type of organic EL devices has been studied. It is known that, due to emission characteristics, a highly efficient phosphorescent organic EL device cannot be obtained by merely applying a fluorescent device technology. The reason therefor is generally assumed to be as follows.

Specifically, since phosphorescence emission utilizes triplet excitons, a compound used for forming an emitting layer is required to have a large energy gap. This is because the energy gap (hereinafter often referred to as "singlet energy") of a compound is normally larger than the triplet energy (in the invention, the triplet energy means the difference in energy between the lowest excited triplet state and the ground state) of the compound.

In order to efficiently confine the triplet energy of the phosphorescent dopant material in the emitting layer, it is required to use a host material having a triplet energy larger than the triplet energy of the phosphorescent dopant material in the emitting layer.

In order to reduce the driving voltage of an organic EL device, it is necessary to use a material having excellent charge-injecting properties or charge-transporting properties. However, when a material that is excellent in charge-injecting properties or charge-transporting properties is used, while the driving voltage is lowered, charge balance in an emitting layer may be deteriorated, thus leading to shortened lifetime of a device. That is, a charge-transporting material that is capable of decreasing the driving voltage while keeping the lifetime of a device long is required.

For the reasons mentioned above, in order to improve performance of a phosphorescent organic EL device, material selection and device design different from those of a fluorescent organic EL device are required.

Intensive studies have been made on materials, and several reports were made.

Patent Document 1 discloses a polycyclic compound as a material for an organic EL device. Specifically, it discloses a compound in which polycyclic compounds are bonded through a linking group.

Patent Document 2 discloses, as a material for an organic EL device, a compound in which indolocarbazole skeletons are bonded through an aromatic hydrocarbon group or the like having a structure different from a fused ring structure as a linking group.

RELATED ART DOCUMENT

Patent Document

Patent Document 1
  WO2009/148016
Patent Document 2
  WO2007/063754

SUMMARY OF THE INVENTION

An object of the invention is to provide a compound that can contribute to a decrease in driving voltage and an increase in efficiency of an organic EL device.

According to one aspect of the invention, the following compound is provided.

A compound that comprises two or more structures represented by the following formula (1) in the same molecule and in which at least two of the structures represented by the formula (1) are directly bonded to each other by a single bond:

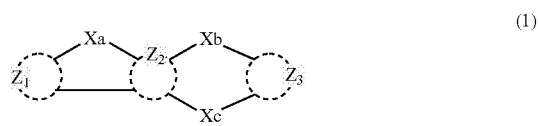

(1)

wherein in the formula (1),
  Xa is O, S, N(R) or C(R1a)(R1b);
  Xb and Xc are independently O, S, N(R), C(R1a)(R1b) or a single bond, provided that at least one of Xb and Xc is a single bond;
  R is a single bond, a hydrogen atom, a substituted or unsubstituted alkyl group including 1 to 30 carbon atoms, a substituted or unsubstituted cycloalkyl group including 3 to 30 carbon atoms that form a ring (hereinafter referred to as "ring carbon atoms"), a substituted or unsubstituted aromatic hydrocarbon ring group including 6 to 30 ring carbon atoms or a substituted or unsubstituted aromatic heterocyclic group including 3 to 30 atoms that form a ring (hereinafter referred to as "ring atoms");
  R1a and R1b are independently a hydrogen atom, a substituted or unsubstituted alkyl group including 1 to 30 carbon atoms, a substituted or unsubstituted cycloalkyl group including 3 to 30 ring carbon atoms, a substituted or unsubstituted aromatic hydrocarbon ring group including 6 to 30 ring carbon atoms or a substituted or unsubstituted aromatic heterocyclic group including 3 to 30 ring atoms;
  provided that there is no case that both of Xa and Xb, or both of Xa and Xc are C(R1a)(R1b), and there is no case that both of Xa and Xb, or both of Xa and Xc are N(R);
  $Z_1$, $Z_2$ and $Z_3$ are independently a substituted or unsubstituted aromatic hydrocarbon ring group including 6 to 30 ring carbon atoms or a substituted or unsubstituted aromatic heterocyclic group including 3 to 30 ring atoms;
  provided that the two or more structures represented by the formula (1) may be the same as or different from each other.

According to the invention, it is possible to provide a compound that can contribute to a decrease in driving voltage and an increase in efficiency of an organic EL device.

BRIEF DESCRIPTION OF THE DRAWINGS

FIG. 1 is a schematic view showing a layer configuration of one embodiment of an organic EL device according to one aspect of the invention,

MODE FOR CARRYING OUT THE INVENTION

A compound according to one aspect of the invention comprises two or more structures represented by the following formula (1) in the same molecule and in which at least two of the structures represented by the formula (1) are directly bonded to each other by a single bond:

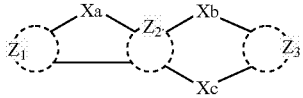
(1)

wherein in the formula (1),

Xa is O, S, NR or C(R1a)(R1b);

Xb and Xc are independently O, S, NR, C(R1a)(R1b) or a single bond, provided that at least one of Xb and Xc is a single bond;

R is a single bond, a hydrogen atom, a substituted or unsubstituted alkyl group including 1 to 30 carbon atoms, a substituted or unsubstituted cycloalkyl group including 3 to 30 ring carbon atoms, a substituted or unsubstituted aromatic hydrocarbon ring group including 6 to 30 ring carbon atoms or a substituted or unsubstituted aromatic heterocyclic group including 3 to 30 ring atoms;

R1a and R1b are independently a hydrogen atom, a substituted or unsubstituted alkyl group including 1 to 30 carbon atoms, a substituted or unsubstituted cycloalkyl group including 3 to 30 ring carbon atoms, a substituted or unsubstituted aromatic hydrocarbon ring group including 6 to 30 ring carbon atoms or a substituted or unsubstituted aromatic heterocyclic group including 3 to 30 ring atoms;

provided that there is no case that both of Xa and Xb, or both of Xa and Xc are C(R1a)(R1b), and there is no case that both of Xa and Xb, or both of Xa and Xc are N(R);

$Z_1$, $Z_2$ and $Z_3$ are independently a substituted or unsubstituted aromatic hydrocarbon ring group including 6 to 30 ring carbon atoms or a substituted or unsubstituted aromatic heterocyclic group including 3 to 30 ring atoms;

provided that the two or more structures represented by the formula (1) may be the same as or different from each other.

The compound according to one aspect of the invention is expected to realize low driving voltage when used as a material for an organic EL device since it has a structure in which highly planar polycyclic hetero-aromatic rings are directly bonded to each other.

Further, the compound according to one aspect of the invention is a compound that is suited as a material for a short-wavelength phosphorescent device since triplet energy can be kept high due to a structure in which polycyclic hetero-aromatic rings having a wide gap are directly bonded to each other without presence of an aromatic ring as a linking group.

The compound according to one aspect of the invention is preferably a compound represented by any of the following formulas (1a) to (1e):

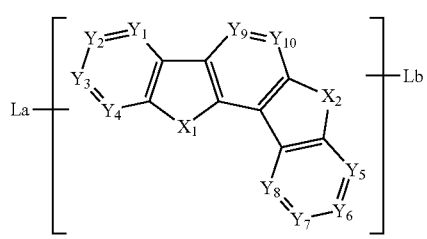
(1a)

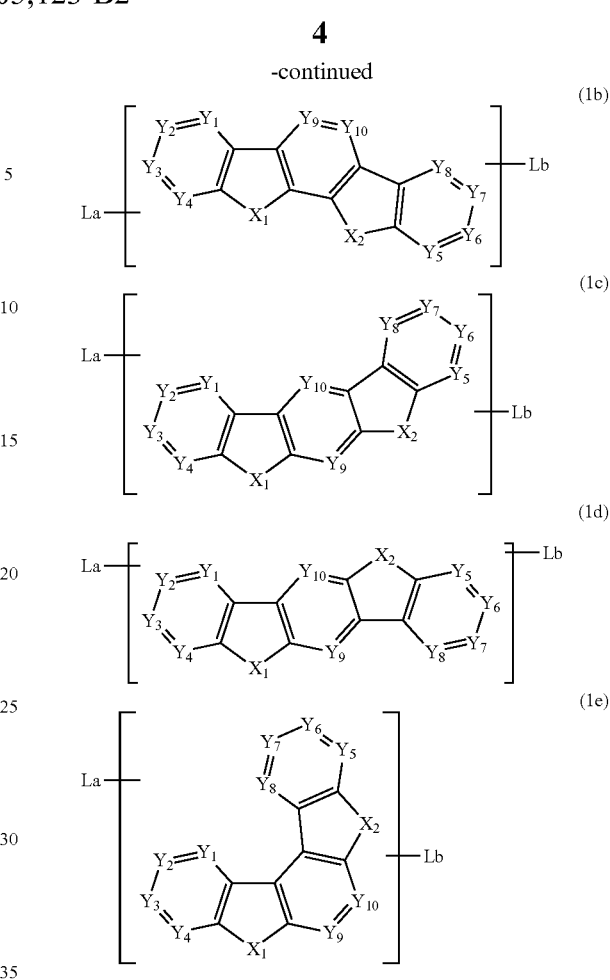

wherein in the formulas (1a), (1b), (1c), (1d) and (1e), La and Lb are independently any of the structures represented by the following formulas (a) to (e);

$X_1$ and $X_2$ are independently O, S, N(R) or C(R1a)(R1b);

$Y_1$ to $Y_{10}$ are independently C(R1) or a nitrogen atom;

R and R1 are independently a single bond, a hydrogen atom, a substituted or unsubstituted alkyl group including 1 to 30 carbon atoms, a substituted or unsubstituted cycloalkyl group including 3 to 30 ring carbon atoms, a substituted or unsubstituted aromatic hydrocarbon ring group including 6 to 30 ring carbon atoms or a substituted or unsubstituted aromatic heterocyclic group including 3 to 30 ring atoms;

R1s that bond to adjacent carbon atoms may be bonded to each other to form a ring;

R1a and R1b are independently a hydrogen atom, a substituted or unsubstituted alkyl group including 1 to 30 carbon atoms, a substituted or unsubstituted cycloalkyl group including 3 to 30 ring carbon atoms, a substituted or unsubstituted aromatic hydrocarbon ring group including 6 to 30 ring carbon atoms or a substituted or unsubstituted aromatic heterocyclic group including 3 to 30 ring atoms;

both of La and Lb independently bond to any of $X_1$ to $X_2$ and $Y_1$ to $Y_{10}$ or one of La and Lb bonds to any of $X_1$ to $X_2$ and $Y_1$ to $Y_{10}$, the other of La and Lb bonds to Lc; and Lc bonds to any of $X_1$ to $X_2$ and $Y_1$ to $Y_{10}$;

Lc is a substituted or unsubstituted aromatic hydrocarbon ring group including 6 to 30 ring carbon atoms or a substituted or unsubstituted aromatic heterocyclic group including 3 to 30 ring atoms;

any two of $X_1$ to $X_2$ and $Y_1$ to $Y_{10}$ are any selected from N(R) in which R is a single bond and C(R1) in which R1 is a single bond, and the single bonds serve as an atomic bonding with any two of La, Lb and Lc;

provided that there is no case that both of $X_1$ and $X_2$ are $C(R1a)(R1b)$ and there is no case that both of $X_1$ and $X_2$ are $N(R)$;

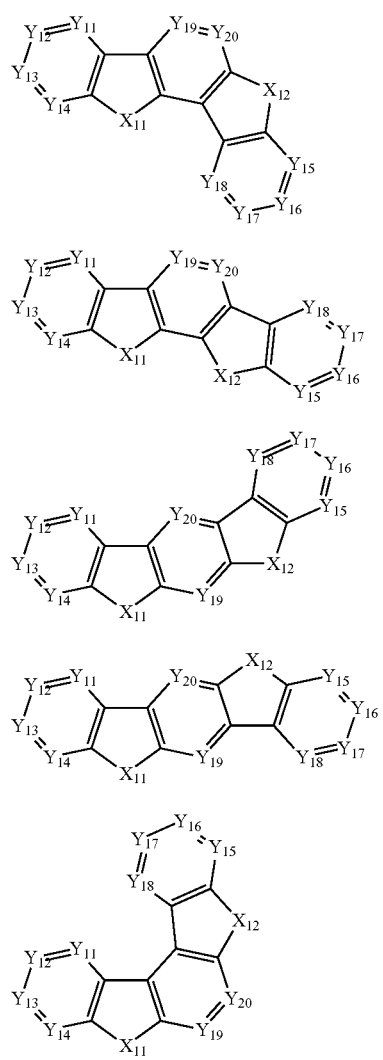

wherein in the formulas (a), (b), (c), (d) and (e), $X_{11}$ and $X_{12}$ are the same as $X_1$ and $X_2$ in the formulas (1a) to (1e), respectively;

$Y_{11}$ to $Y_{20}$ are the same as $Y_1$ to $Y_{10}$ in the formulas (1a) to (1e), respectively; and at least one of $X_{11}$ to $X_{12}$ and $Y_{11}$ to $Y_{20}$ bonds to a structure represented by the formulas (1a) to (1e).

$X_1$ and $X_2$ and $Y_1$ to $Y_{10}$ in the formulas (1a) to (1e) and $X_{11}$ and $X_{12}$ and $Y_{11}$ to $Y_{20}$ in the formulas (a) to (e) may be the same as or different from each other, respectively.

For example, if the compound according to one aspect of the invention is a compound represented by the formula (1a) and La is a structure represented by the formula (a) and Lb is a structure represented by the formula (b), $X_1$ in the formula (1a), $X_{11}$ in the formula (a) and $X_{11}$ in the formula (b) may be the same as or different from each other.

In the above formulas (1a) to (1e), it is preferred that La and Lb respectively bond to any of $X_1$ to $X_2$ and $Y_1$ to $Y_{10}$.

In the above formulas (1a) to (1e), it is preferred that one of $X_1$ and $X_2$ be $N(R)$ and the other of $X_1$ and $X_2$ be an oxygen atom or a sulfur atom.

In the above formulas (1a) to (1e), it is preferred that $X_1$ and $X_2$ be independently an oxygen atom or a sulfur atom.

In the formulas (1a) to (1e), it is preferred that at least one of La and Lb be a structure represented by any of the following structures (f) to (j):

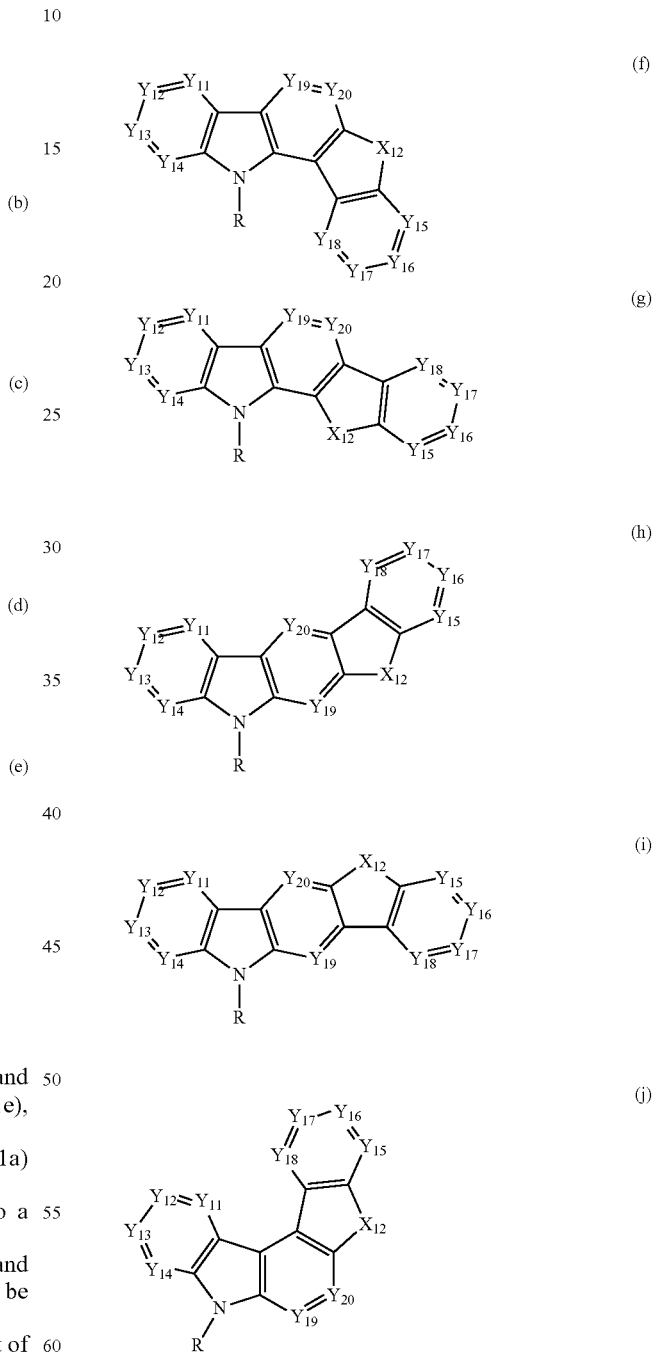

In the formulas (f) to (j), $X_{12}$, R, and $Y_{11}$ to $Y_{20}$ are the same as those in the formulas (a) to (e).

The compound according to one aspect of the invention is preferably a compound represented by the following formula (2).

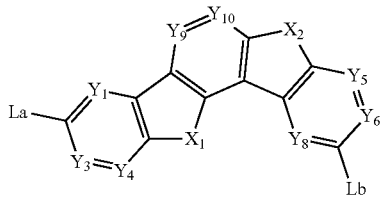

(2)

wherein in the formula (2), $X_1$, $X_2$, $Y_1$, $Y_3$ to $Y_6$, $Y_8$ to $Y_{10}$, La and Lb are the same as those in the above formulas (1a) to (1e).

In the formula (2), it is preferred that at least one of La and Lb be any of the structures represented by the formulas (f) to (j).

In the formula (2), it is preferred that both La and Lb be independently represented by any of the formulas (f) to (j), and that the Rs be both a single bond and bond to a carbon atom present in a part indicated by * in the formula (2a):

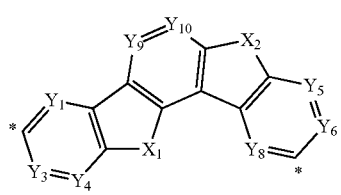

(2a)

wherein in the formula (2a), $X_1$, $X_2$, $Y_1$ to $Y_6$, $Y_8$ to $Y_{10}$, La and Lb are the same as those in the above formula (2).

Hereinbelow, an explanation will be made on each group in the above-mentioned formula (1), or the like.

In the invention, the "unsubstituted" in the "substituted or unsubstituted . . . " means that a hydrogen atom is bonded. The "hydrogen atom" includes isomers differing in number of neutrons, i.e. protium, deuterium and tritium.

The "carbon atoms that form a ring" means carbon atoms that constitute a saturated ring, an unsaturated ring or an aromatic ring. The "atoms that form a ring" means carbon atoms and hetero atoms that constitute a heterocycle (including a saturated ring, an unsaturated ring and an aromatic ring).

In addition, Lc is a linking group of La and Lb, and $X_1$ to $X_2$ and $Y_1$ to $Y_{10}$. As examples of the aromatic hydrocarbon ring group and the aromatic heterocyclic group of Lc, residues corresponding to specific examples mentioned later can be given.

As specific examples of the aromatic hydrocarbon ring group (aryl group), phenyl, tolyl, xylyl, naphthyl, phenanthryl, pyrenyl, chrysenyl, benzo[c]phenanthryl, benzo[g]chrysenyl, benzoanthryl, triphenylenyl, fluorenyl, 9,9-dimethylfluorenyl, benzofluorenyl, dibenzofluorenyl, biphenyl, terphenyl, fluoranthenyl or the like can be given, with phenyl, biphenyl and naphthyl being preferable.

As the aromatic hydrocarbon group having a substituent, a tolyl group, a xylyl group, a 9,9-dimethylfluorenyl group or the like can be given.

As shown by the specific examples, the aryl group includes both fused aryl groups and non-fused aryl groups.

As specific examples of the aromatic heterocyclic group (heteroaryl group, heteroaromatic ring group, heterocyclic group), a pyrrolyl group, a pyrazolyl group, a pyrazinyl group, a pyrimidinyl group, a pyridazinyl group, a pyridyl group, a triazinyl group, an indolyl group, an isoindolyl group, an imidazolyl group, a benzimidazolyl group, an indazolyl group, an imidazo[1,2-a]pyridinyl group, a furyl group, a benzofuranyl group, an isobenzofuranyl group, a dibenzofuranyl group, an azadibenzofuranyl group, a thiophenyl group, a benzothiophenyl group, a dibenzothiophenyl group, an azadibenzothiophenyl group, a quinolyl group, an isoquinolyl group, a quinoxalinyl group, a quinazolinyl group, a naphthyridinyl group, a carbazolyl group, an azacarbazolyl group, a phenanthridinyl group, an acridinyl group, a phenanthrolinyl group, a phenazinyl group, a phenothiazinyl group, a phenoxazinyl group, an oxazolyl group, an oxadiazolyl group, a furazanyl group, a benzoxazolyl group, a thienyl group, a thiazolyl group, a thiadiazolyl group, a benzothiazolyl group, a triazolyl group, a tetrazolyl group or the like can be given. A dibenzofuranyl group, a dibenzothiophenyl group and a carbazolyl group can preferably be given.

The above azacarbazolyl group is an azacarbazolyl group including 2 to 5 nitrogen atoms, for example, and a monovalent group derived from the following azacarbazole can be given. The atomic bonding may be present at any of nitrogen atoms and at any of carbon atoms. Further, any of nitrogen atoms and any of carbon atoms may be substituted.

As the alkyl group, a straight-chain, branched or cyclic alkyl group can be given. As the straight-chain or branched alkyl group, a methyl group, an ethyl group, a propyl group, an isopropyl group, a n-butyl group, an isobutyl group, a sec-butyl group, a tert-butyl group, a n-pentyl group, a n-hexyl group, a n-heptyl group, a n-octyl group or the like can be given. A methyl group, an ethyl group, a propyl group, an isopropyl group, a n-butyl group, an isobutyl group, a sec-butyl group and a tert-butyl group can be given. A methyl group, an ethyl group, a propyl group, an isopropyl group, a n-butyl group, a s-butyl group and a t-butyl group are further preferable.

As the cycloalkyl group, a cyclopropyl group, a cyclobutyl group, a cyclopentyl group, a cyclohexyl group, a 1-adamantyl group, a 2-adamantyl group, a 1-norbornyl group, a 2-norbornyl group or the like can be given. A cydopentyl group and a cyclohexyl group are preferable.

Specific examples of the compound according to one aspect of the invention are given below. The compounds according to one aspect of the invention are not restricted to the following examples.

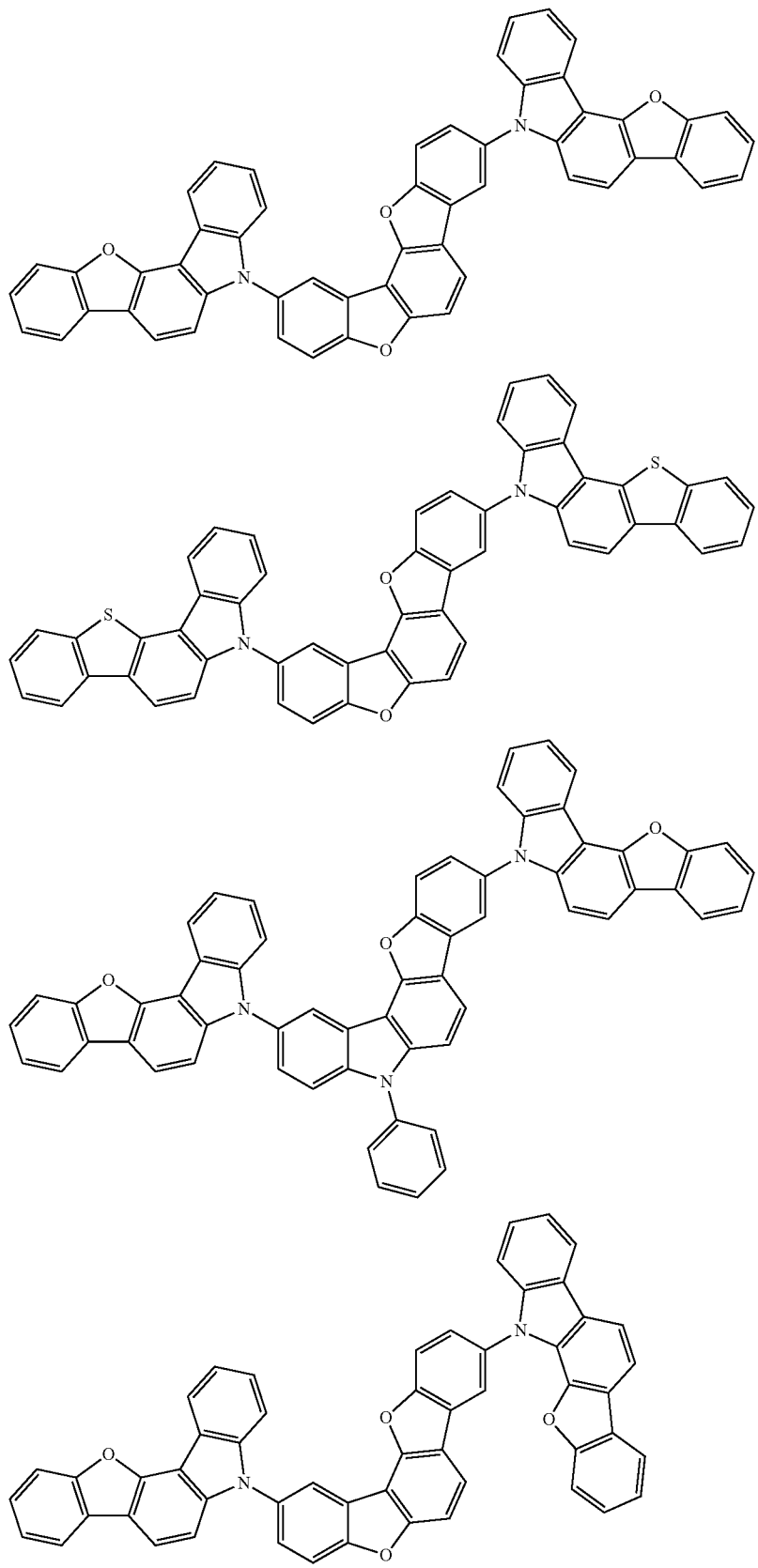

-continued
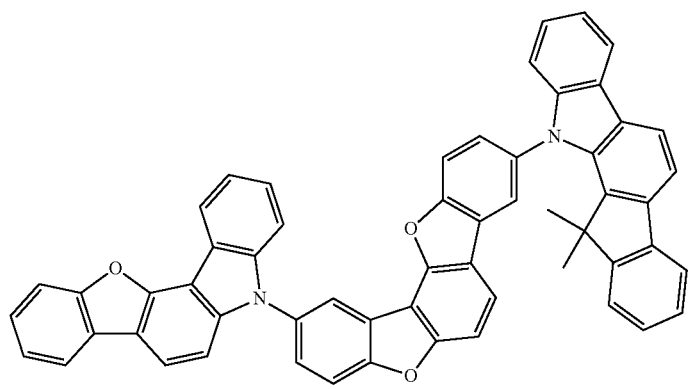
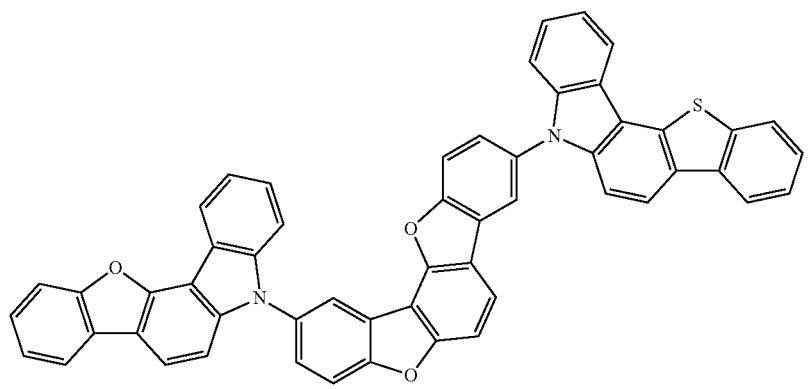
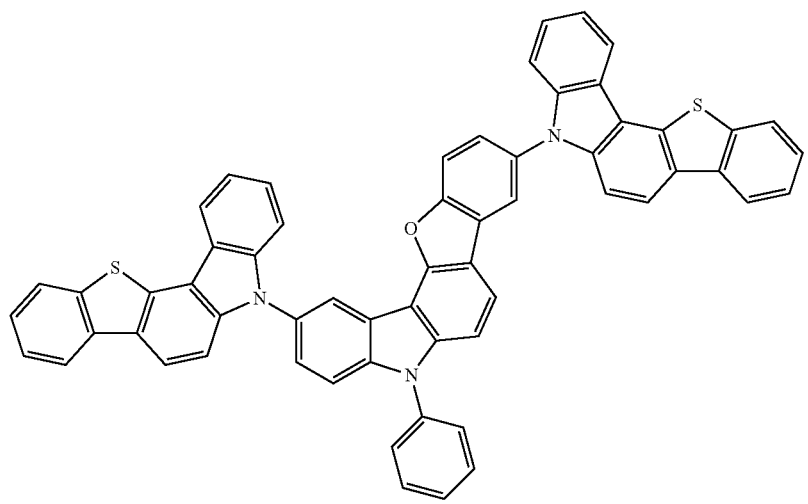

-continued
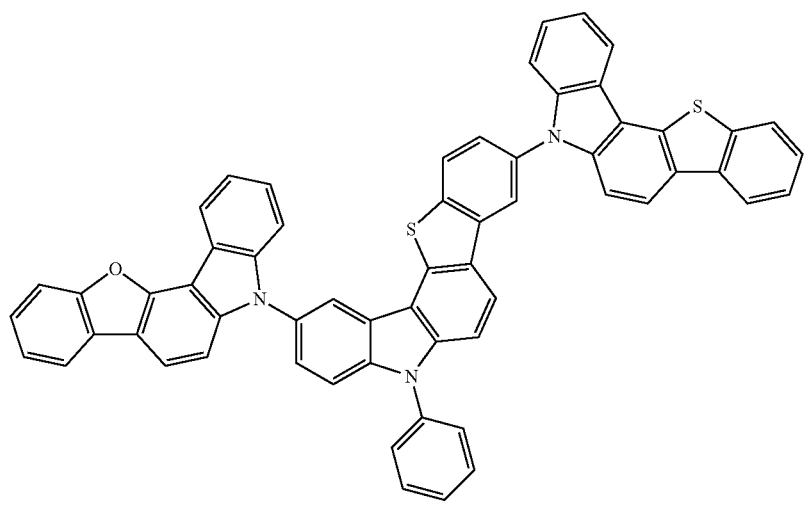
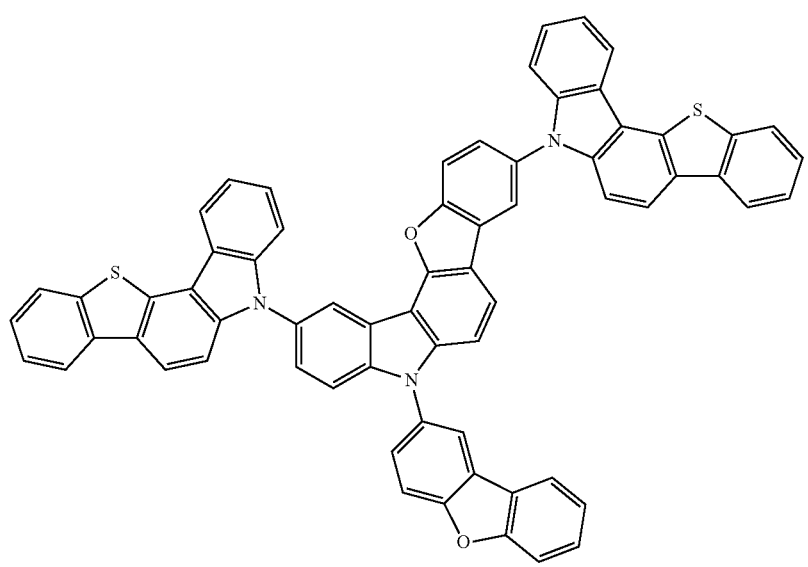
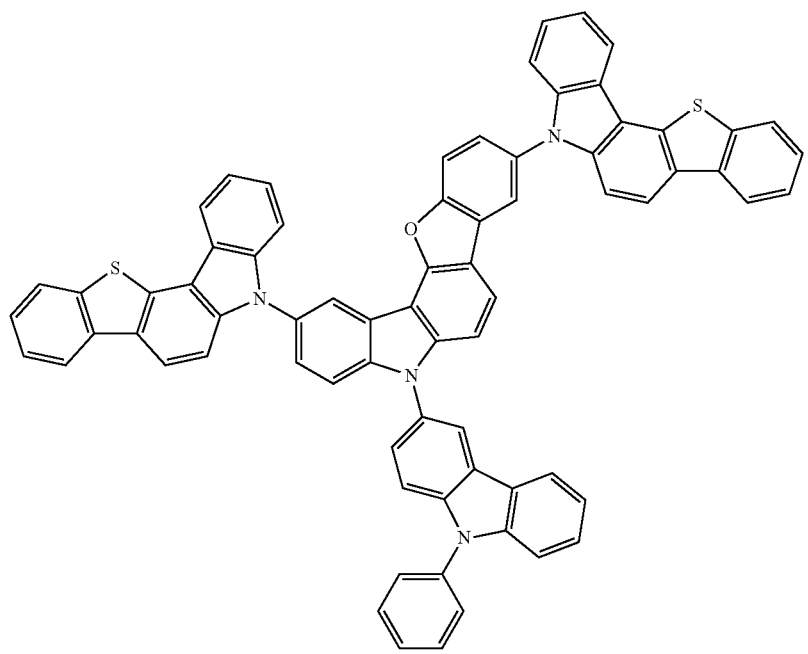

-continued
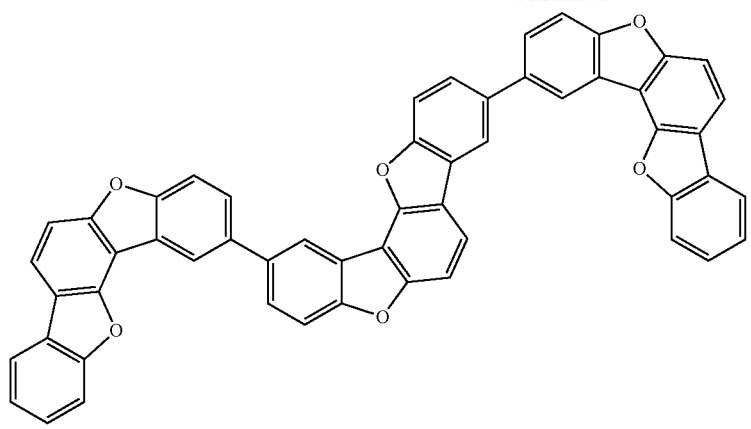
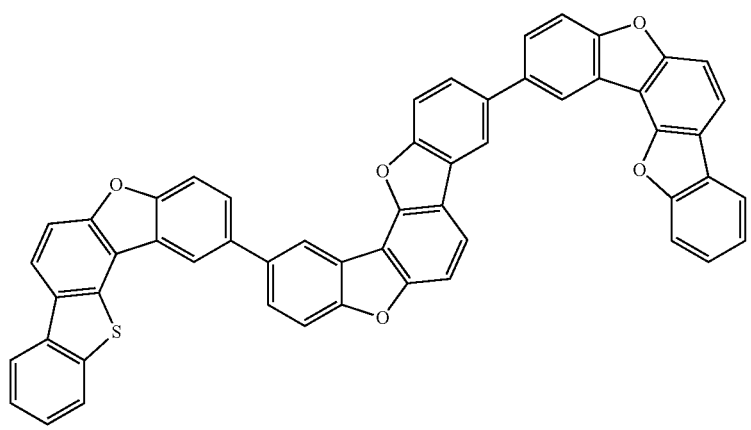
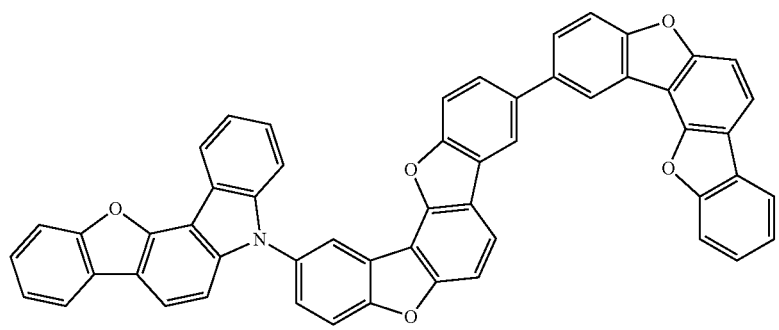
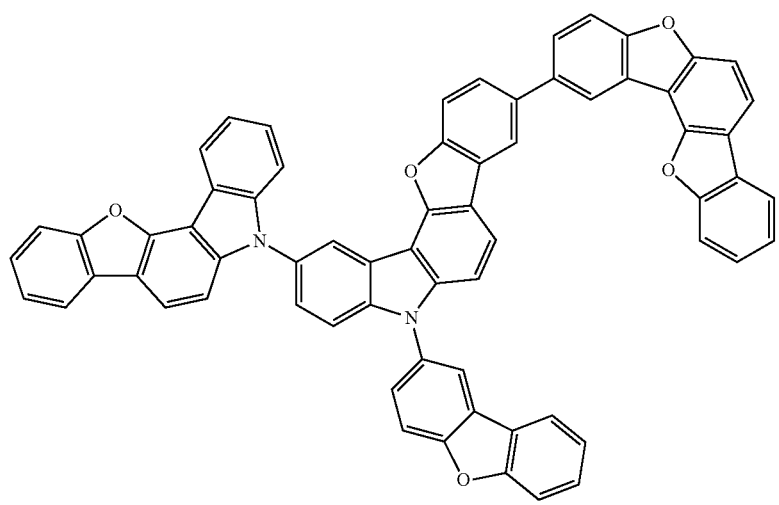

-continued
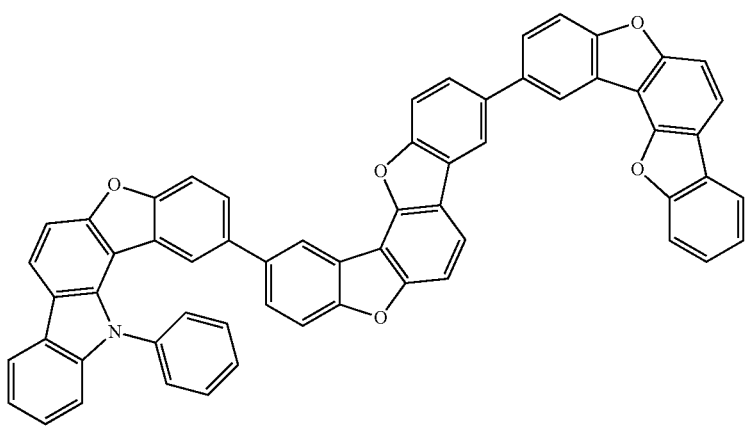
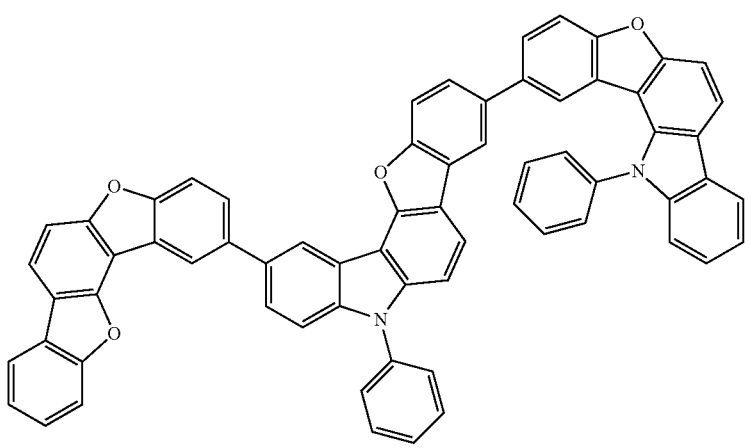
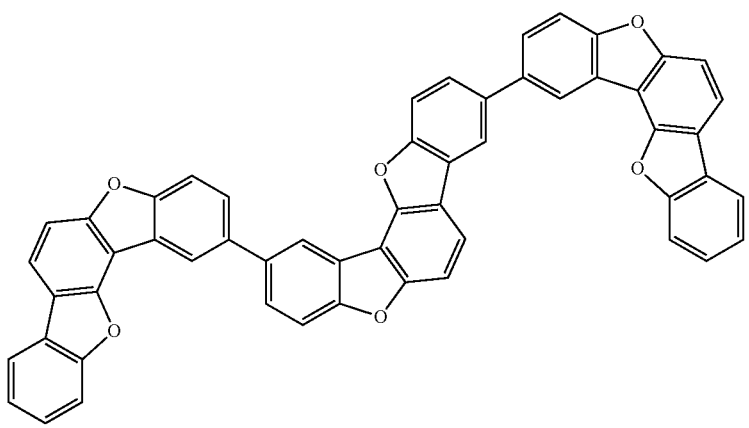

-continued
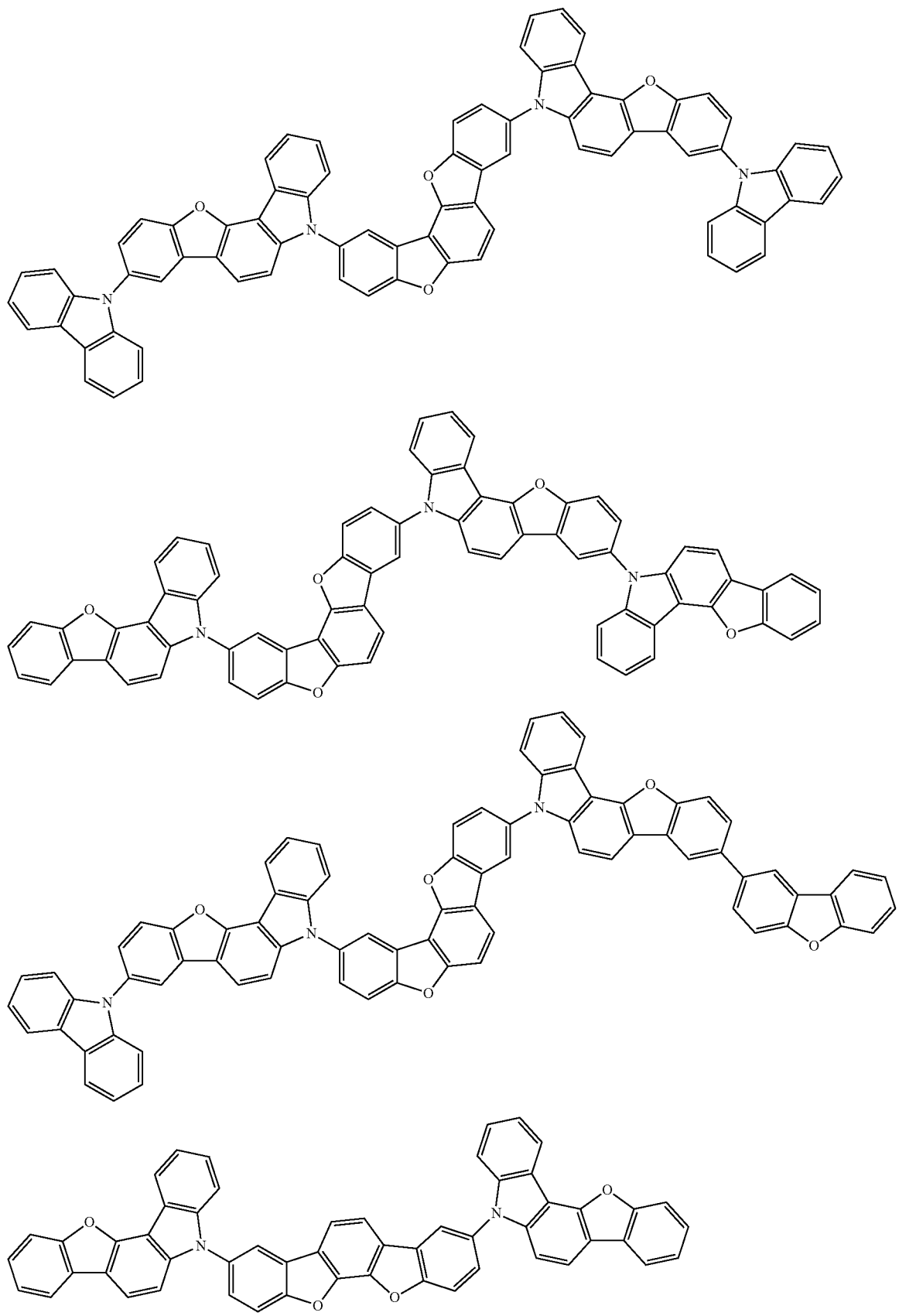

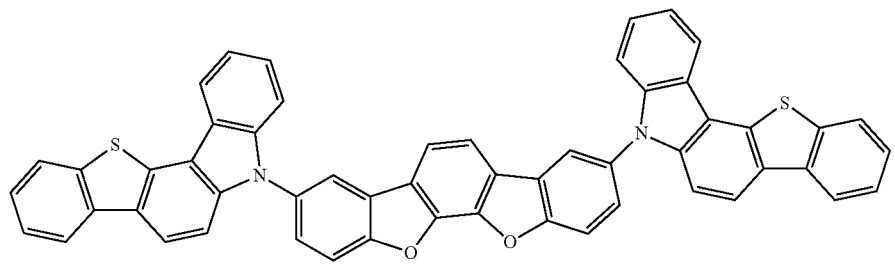
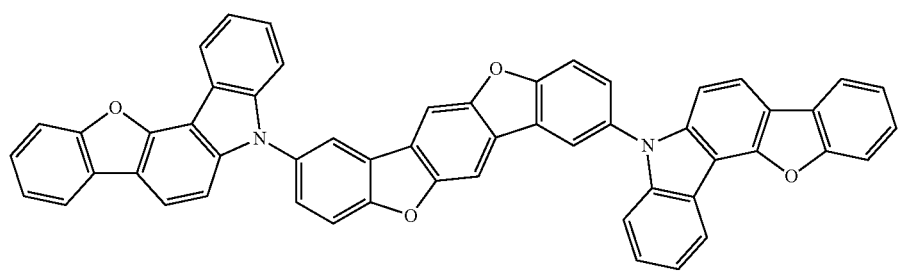
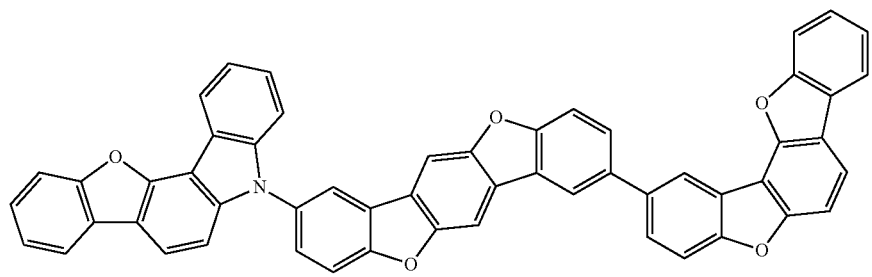
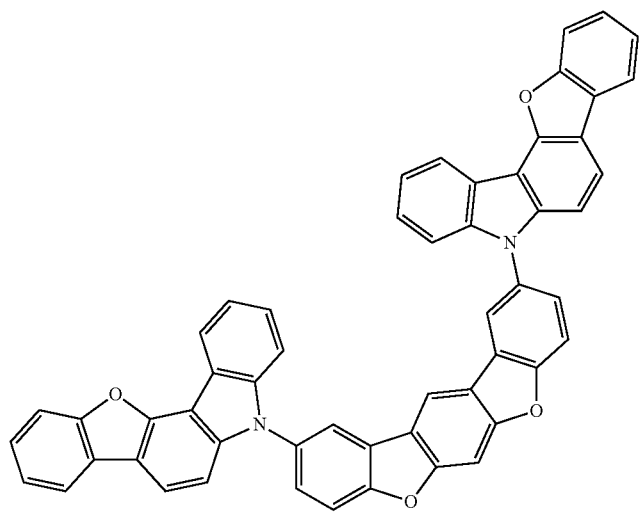

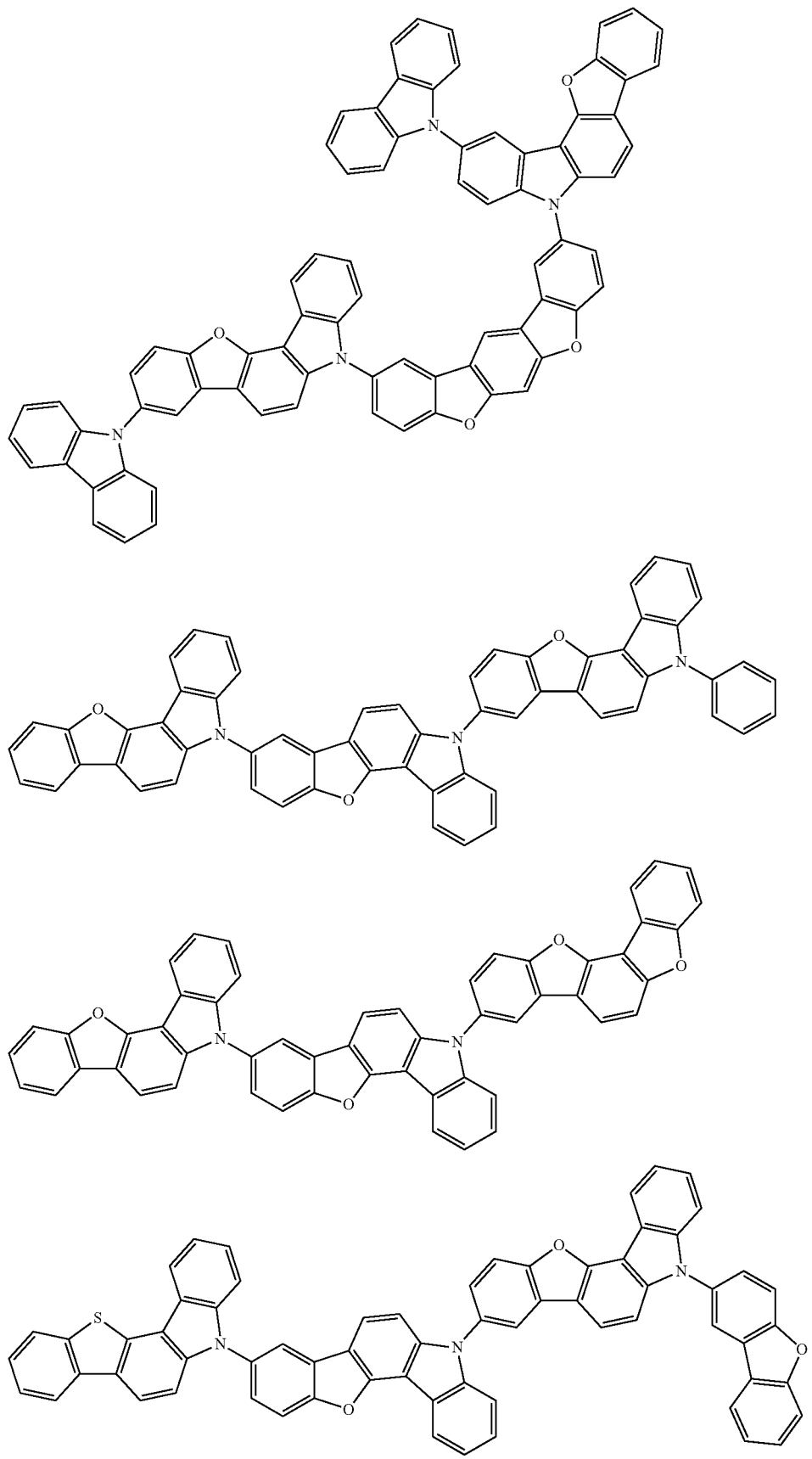

-continued
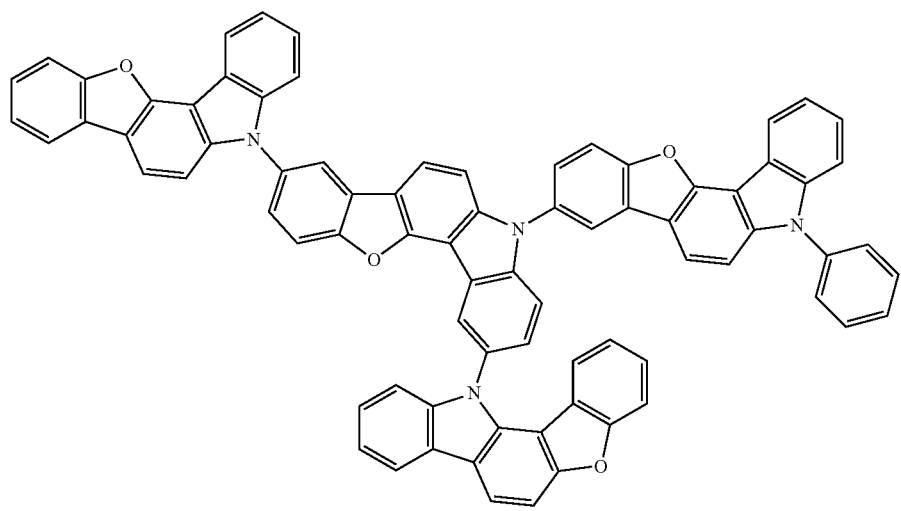
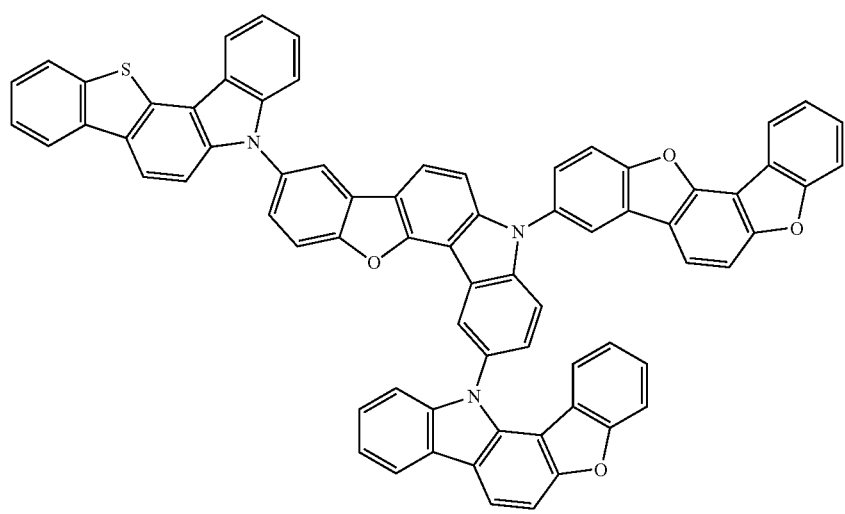
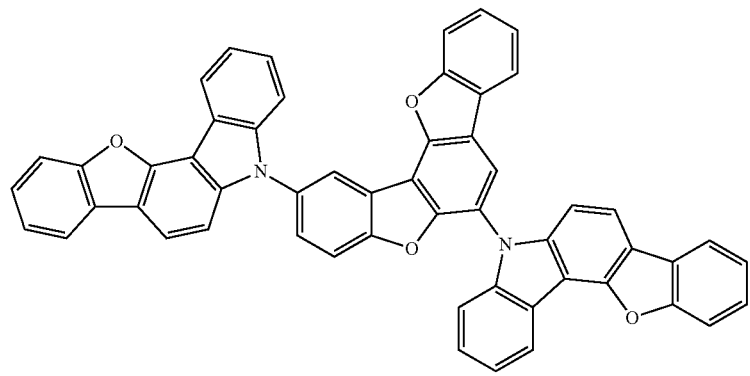

-continued
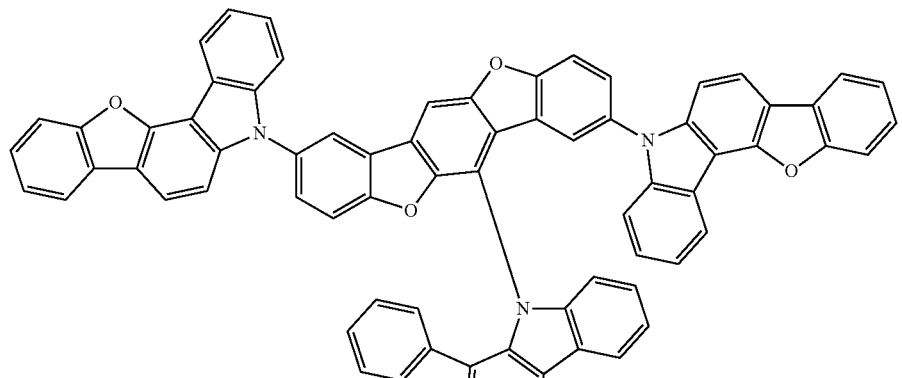
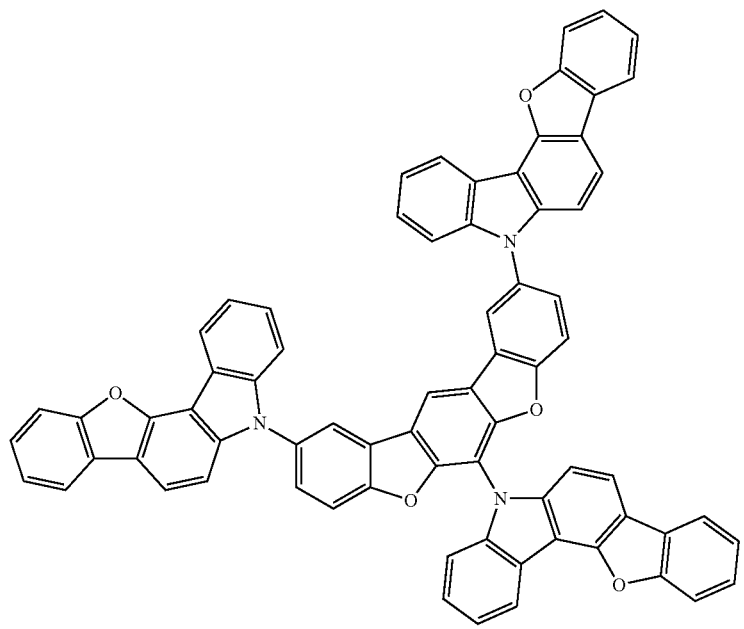
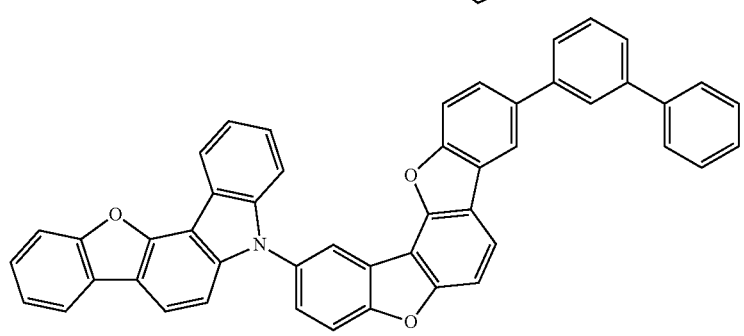
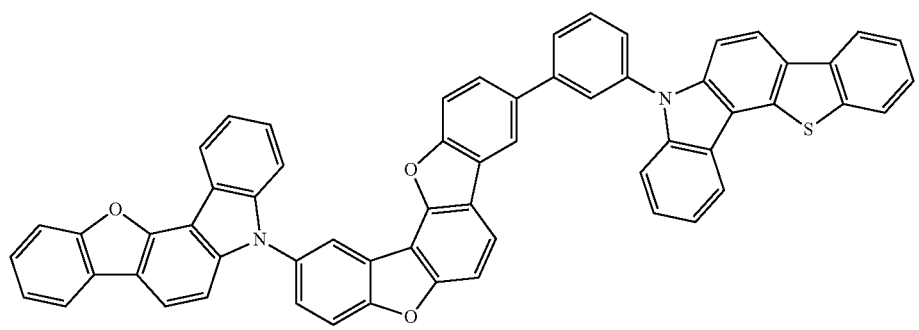

-continued
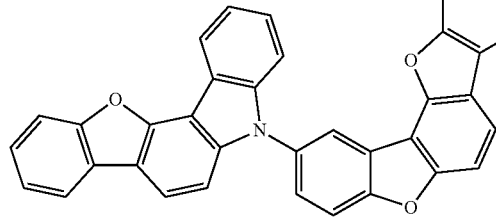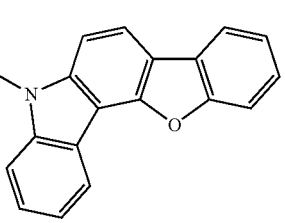
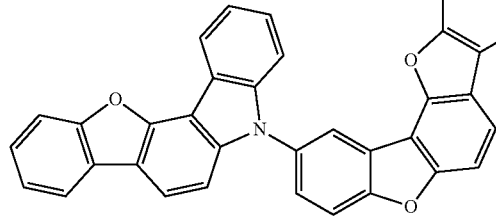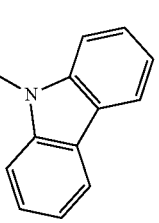
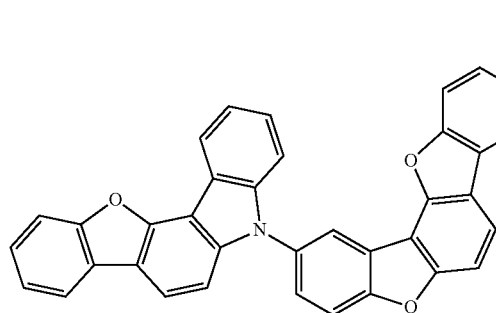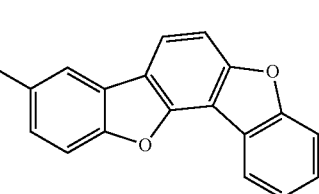
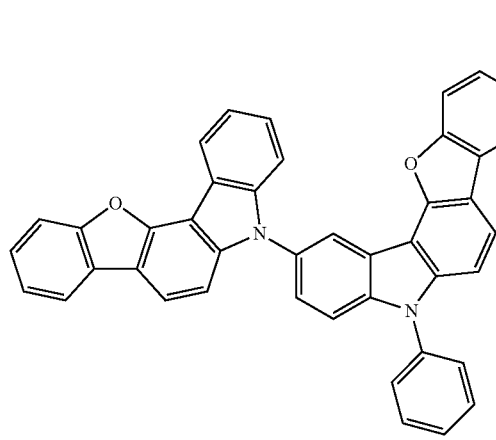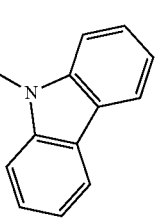

-continued
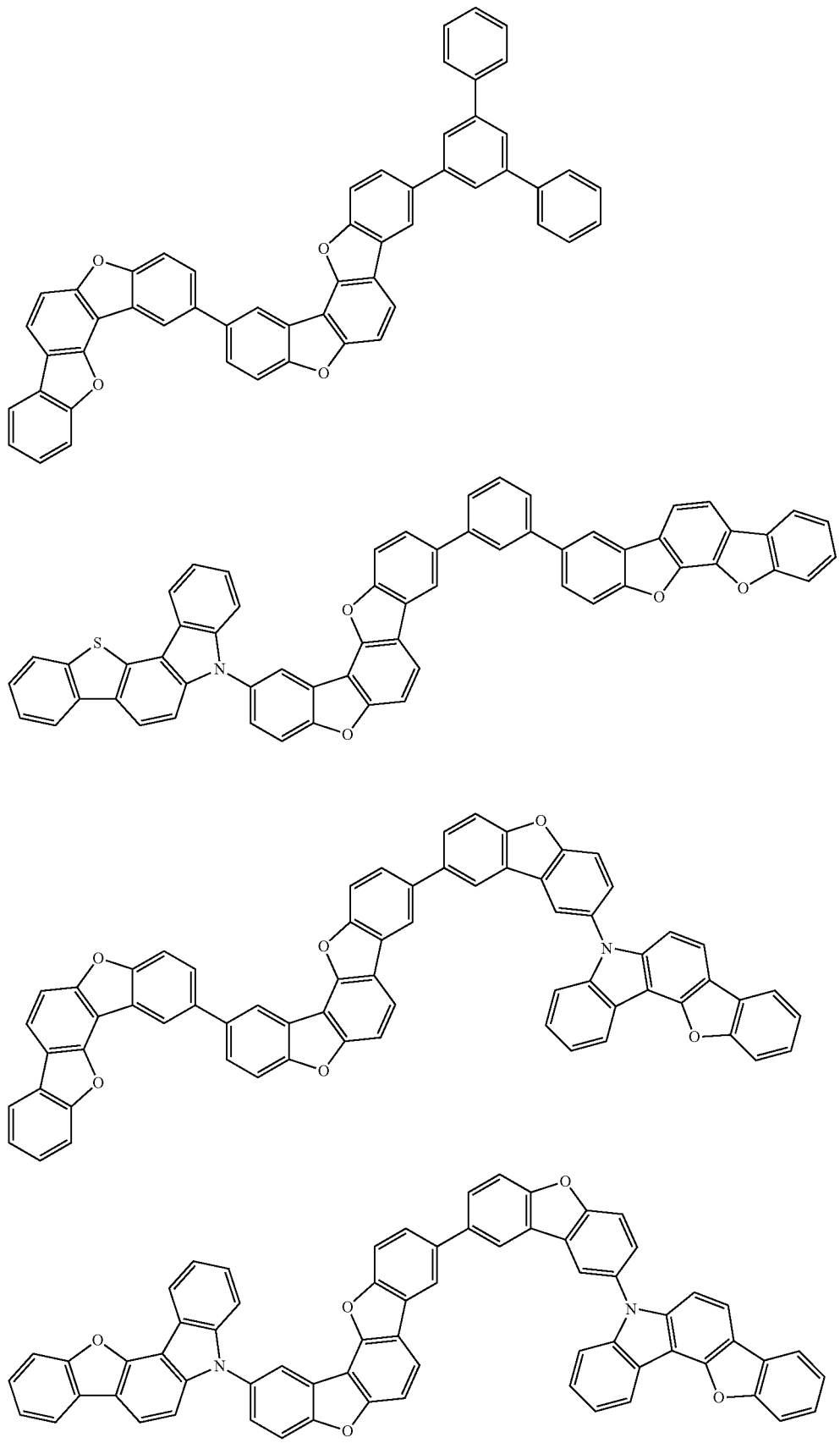

-continued
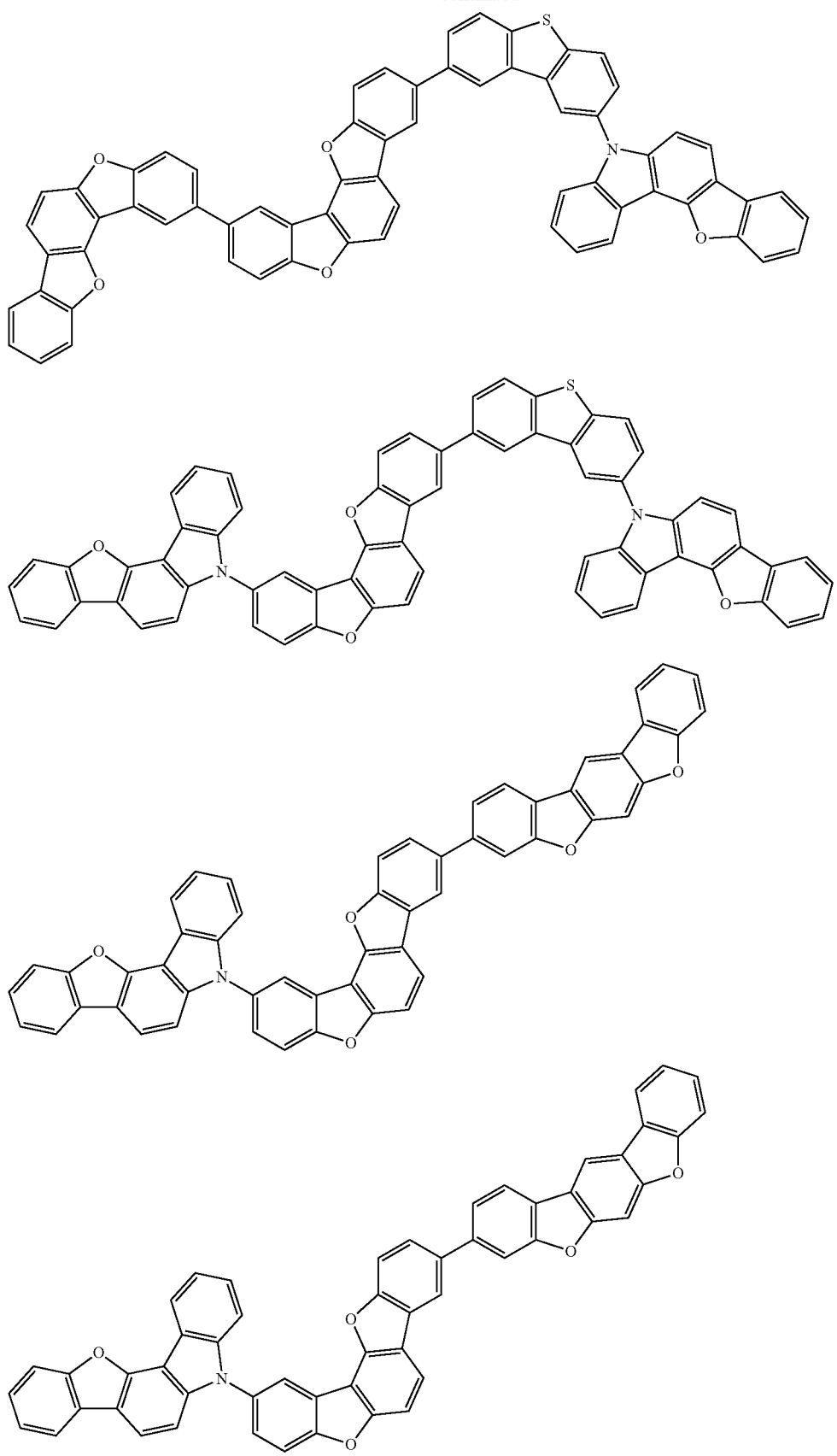

-continued
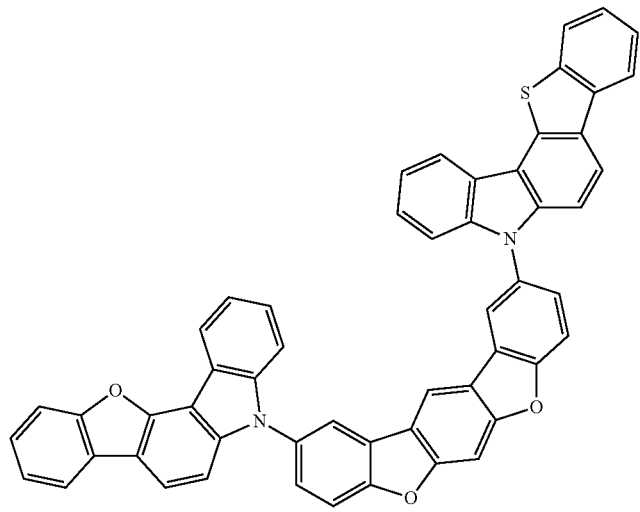
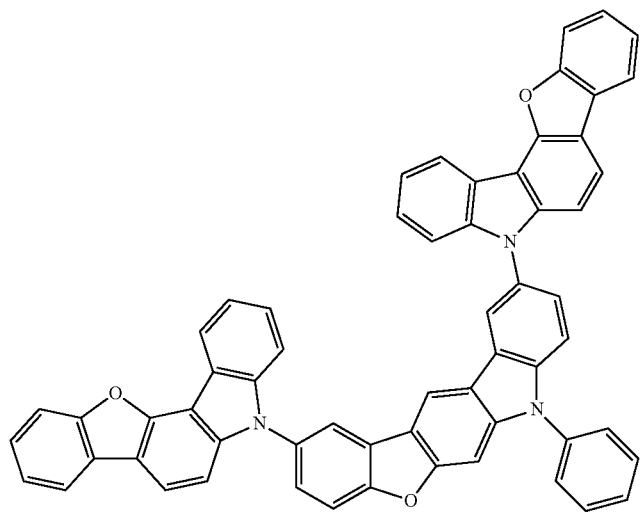
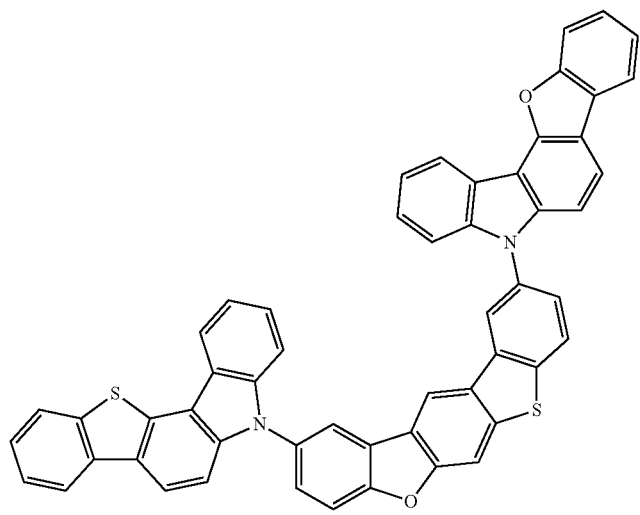

-continued

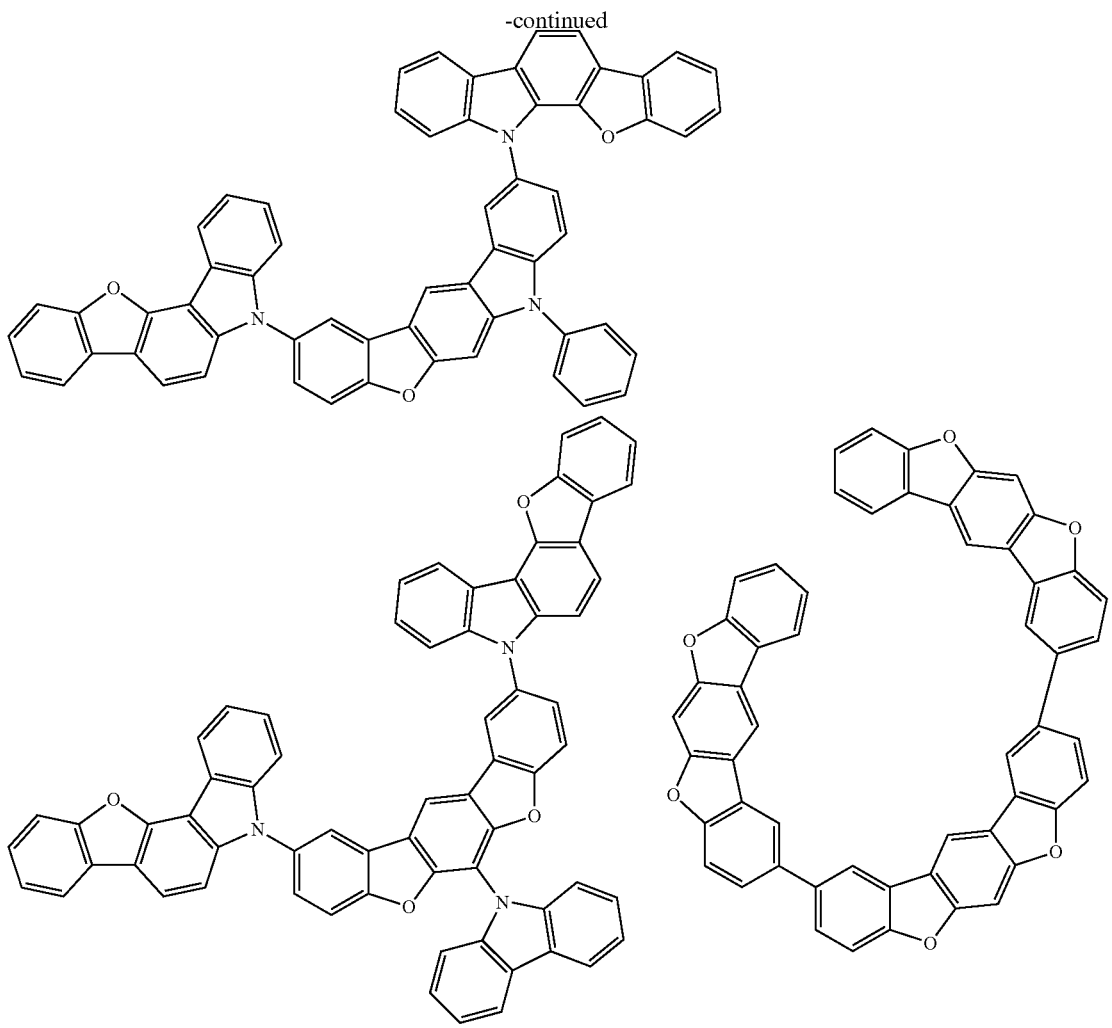

The compound according to one aspect of the invention can be used as a material for an organic EL device, can be preferably used as a material in an emitting layer of an organic EL device, and can be particularly preferably used as a host material of a blue phosphorescent emitting layer. The reason therefor is assumed to be as follows. The compound according to one aspect of the invention has a sufficiently large triplet energy. Therefore, even when a blue phosphorescent emitting dopant material is used, the triplet energy of the phosphorescent emitting dopant material can be efficiently confined within the emitting layer.

The compound according to one aspect of the invention can be used not only in a blue-emitting layer but also in an emitting layer that emits light of a longer wavelength (green to red, etc.).

The material for an organic electroluminescence device according to one aspect of the invention comprises the compound according to one aspect of the invention mentioned above.

[Organic EL Device]

The organic EL device of the invention comprises organic thin film layers including an emitting layer between a cathode and an anode, and at least one layer of these organic thin film layers comprises the compound according to one aspect of the invention (or a material for an organic electroluminescence device according to one aspect of the invention). Due to such a configuration, low-voltage driving of an organic EL device can become possible. Examples of the organic thin film layers include, although not limited thereto, a hole-injecting layer, a hole-transporting layer, an emitting layer, an electron-transporting layer, an electron-injecting layer, a spacing layer, a barrier layer, or the like.

FIG. 1 is a schematic view showing a layer configuration of one embodiment of the organic EL device according to one aspect of the invention.

An organic EL device 1 has a configuration in which, on a substrate 10, an anode 20, a hole-transporting zone 30, an emitting layer 40, an electron-transporting zone 50 and a cathode 60 are stacked in this sequence. The hole-transporting zone 30 is a layer sandwiched between the anode 20 and the emitting layer 40, and means a hole-transporting layer, a hole-injecting layer, an electron-barrier layer, or the like. Similarly, the electron-transporting zone 50 is a layer sandwiched between the cathode 60 and the emitting layer 40, and means an electron-transporting layer, an electron-injecting layer, a hole-barrier layer, or the like. The barrier layers confine electrons or holes in the emitting layer 40, and can increase the possibility of generation of excitons in the emitting layer 40. These barrier layers may not necessarily be formed, but it is preferred that one or more barrier layers be formed. In this device, the organic thin film layer is each organic layer formed in the hole-transporting zone 30, the emitting layer 40 and each layer formed in the electron-transporting zone 50.

Hereinbelow, an explanation will be made on a material or the like of each layer. The material of each layer is not limited to the materials shown below, and known materials or the like can be used.

[Emitting Layer]

The emitting layer that comprises the compound according to one aspect of the invention preferably comprises a phosphorescent dopant (phosphorescent emitting material).

As the phosphorescent dopant, a metal complex compound can be given. A preferable compound is one having a metal atom selected from Ir, Pt, Os, Au, Cu, Re and Ru and a ligand. It is preferred that the ligand have an ortho-metalated bond.

In respect of high phosphorescent quantum yield and further improvement in external quantum efficiency of an emitting device, it is preferred that the phosphorescent dopant be a compound comprising a metal atom selected from Ir, Os and Pt. The phosphorescent dopant is further preferably a metal complex such as an iridium complex, an osmium complex, a platinum complex or the like. Among these, an iridium complex and a platinum complex are more preferable, with an ortho-metalated iridium complex being most preferable.

The dopant may be used alone or in a mixture of two or more.

The concentration of the phosphorescent dopant added to the emitting layer is not particularly restricted, but preferably 0.1 to 30 mass %, more preferably 0.1 to 20 mass %.

In the emitting layer, a double host (also referred to as a host/cohost) may be used. Specifically, carrier balance in the emitting layer may be adjusted by combining an electron-transporting host and a hole-transporting host in the emitting layer.

A double dopant may be used. In the emitting layer, by using two types of dopant materials having a high quantum yield, each dopant emits light. For example, by co-depositing a host with a red dopant and a green dopant, a yellow light-emitting layer can be realized.

The emitting layer may be either a single layer or a stacked layer structure. By stacking emitting layers, due to accumulation of electrons and holes in the interface of the emitting layer, a recombination region can be concentrated on the emitting layer interface. As a result, quantum efficiency can be increased.

[Blocking Layer]

It is preferred that the compound according to one aspect of the invention be used in a layer adjacent to the emitting layer.

For example, when a layer that is adjacent to the emitting layer 40 (anode-side adjacent layer) in the hole-transporting zone 30 of the device shown in FIG. 1 comprises the compound according to one aspect of the invention, this layer has a function of an electron-barrier layer or an exciton-blocking layer.

When a layer that is adjacent to the emitting layer 40 (a cathode-side adjacent layer) in the electron-transporting zone 50 comprises the compound according to one aspect of the invention, this layer has a function as a hole-barrier layer or an exciton-blocking layer.

The barrier layer (blocking layer) is a layer that has a function as a barrier for movement of carriers or a function as a barrier for diffusion of excitons. Mainly, an organic layer for preventing leakage of electrons from the emitting layer to the hole-transporting zone can be defined as an electron-barrier layer and an organic layer for preventing leakage of holes from the emitting layer to the electron-transporting zone can be defined as a hole-barrier layer. Further, an organic layer for preventing diffusion of triplet excitons generated in the emitting layer to peripheral layers in which the triplet energy has a lower level than that of the emitting layer may be defined as an exciton-blocking layer (triplet barrier layer).

Further, the compound according to one aspect of the invention may be used in a layer that is adjacent to the emitting layer 40, and may be used also in other organic thin film layers that are connected with this adjacent layer.

In addition, when two or more emitting layers are formed, the compound according to one aspect of the invention can be preferably used as a material for a spacing layer formed between the emitting layers.

[Electron-Injecting Layer and Electron-Transporting Layer]

The electron-injecting and transporting layer is a layer that assists injection of electrons into the emitting layer and transports the electrons to the emission region, and has a large electron mobility.

As the electron-transporting material, an aromatic heterocyclic compound having one or more hetero atoms in its molecule is preferably used, and a nitrogen-containing ring derivative is particularly preferable. As the nitrogen-containing ring derivative, an aromatic ring having a nitrogen-containing six-membered or five-membered ring skeleton or a fused aromatic ring compound having a nitrogen-containing six-membered or five-membered ring skeleton is preferable. For example, a compound having in its skeleton a pyridine ring, a pyrimidine ring, a triazine ring, a benzimidazole ring, a phenanthroline ring, a quinazoline ring or the like can be given.

Further, by doping (n) of a donar material or by doping (p) of an acceptor material, an organic layer having semiconductor properties may be formed. Representative examples of N-doping include doping an electron-transporting material with a metal such as Li and Cs. Representative examples of P-doping include doping a hole-transporting material with an acceptor material such as F4TCNQ (2,3,5,6-Tetrafluoro-7,7,8,8-tetracyanoquinodimethane) (see Japan Patent No. 3695714, for example).

In the organic EL device, it is known that, since emitted light is reflected by an electrode (for example, a cathode), emission that is directly outcoupled from an anode and emission that is outcoupled after being reflected by an electrode interfere. In order to utilize this interference efficiently, an electron-injecting and transporting layer is appropriately selected in a thickness range of several nm to several µm. When the film thickness is large, in order to avoid an increase in voltage, it is preferred that the electron mobility be at least $10^{-5}$ cm$^2$/Vs or more when an electrical field of $10^4$ to $10^6$ V/cm is applied.

[Hole-Injecting Layer and Hole-Transporting Layer (Hole-Injecting and Transporting Layer)]

A hole-injecting and transporting layer is a layer that assists injection of holes to the emitting layer and transports the injected holes to an emitting region, and has a large hole mobility and has a small ionization energy (normally, 5.6 eV or less).

An inorganic compound such as p-type Si and p-type SiC can be used as a hole-injecting material.

In the material for the hole-injecting and transporting layer, a cross-linkable material can be used.

[Substrate]

As the substrate, a glass plate, a polymer plate or the like can be used.

Examples of the glass plate include a plate of soda-lime glass, barium/strontium-containing glass, lead glass, aluminosilicate glass, borosilicate glass, barium borosilicate glass, quartz or the like. Examples of the polymer plate include a plate of polycarbonate, acrylic resins, polyethylene terephthalate, polyethersuffone, polysulfone, or the like.

[Anode]

The anode is formed of a conductive material, for example, and one having a work function larger than 4 eV is suitable.

As the conductive material, carbon, aluminum, vanadium, iron, cobalt, nickel, tungsten, silver, gold, platinum and palladium, alloys thereof, metal oxides such as tin oxide and indium oxide which are used for an ITO substrate and a NESA substrate and an organic conductive resin such as polythiophene and polypyrrole are used.

If necessary, the anode may be formed of two or more layers.

[Cathode]

The cathode is formed of a conductive material, for example, and one having a work function smaller than 4 eV is suitable.

As the conductive material, magnesium, calcium, tin, lead, titanium, yttrium, lithium, ruthenium, manganese, aluminum and lithium fluoride, and alloys thereof are used, but usable materials are not limited thereto.

Representative examples of the alloy include, though not limited thereto, a magnesium/silver alloy, a magnesium/indium alloy and a lithium/aluminum alloy. The amount ratio of an alloy is controlled by the temperature of the deposition source, atmosphere, vacuum degree or the like, and a suitable ratio is selected.

If necessary, the cathode may be formed of two or more layers. This cathode can be formed by making the above-mentioned conductive material into a thin film by vapor deposition, sputtering or some other methods.

In the case where light is outcoupled from the emitting layer through the cathode, the cathode preferably has a light transmittance of larger than 10%.

The sheet resistance of the cathode is preferably several hundreds O/Q or less, and the film thickness thereof is usually from 10 nm to 1 μm, preferably from 50 to 200 nm.

Each layer of the organic EL device of the invention can be formed by a known dry film-forming method such as vacuum vapor deposition, sputtering, plasma coating and ion plating or a known wet film-forming method such as spin coating, dipping and flow coating.

Although no particular restrictions are imposed on the film thickness of each layer, it is required to set it to a suitable film thickness. If the film thickness is too large, a large voltage is required to be applied in order to obtain a certain optical output, resulting in poor efficiency. If the film thickness is too small, pinholes or the like are generated, and hence, a sufficient luminance cannot be obtained even if an electric field is applied. The film thickness is normally in the range of 5 nm to 10 μm, with the range of 10 nm to 0.2 μm being further preferable.

EXAMPLES

Synthesis of Hetero-Fused Ring-Connected Compound

Example 1

Compound A was synthesized by the following method.

(1) Synthesis of Intermediate (1-1)

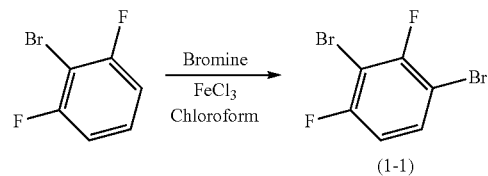 [SMILES: Fc1cccc(F)c1Br ; Fc1ccc(Br)c(F)c1Br]

70 g (363 mmol) of 1,3-difluoro-2-bromobenzene and 11.8 g (72.6 mmol) of iron chloride were added to 350 ml of chloroform, followed by stirring at 0° C. Subsequently, 62.7 g (399 mmol) of bromine was added dropwise, and stirred for 4 hours. 1 L of water was added to the reaction solution, and an organic phase was isolated, and washed with an aqueous sodium hydroxide solution. The solvent was distilled off under reduced pressure. The resulting residues were dissolved in heptane. By purifying with silica gel column chromatography (eluent: heptane alone), 89.1 g of intermediate (1-1) as an intended product was obtained (yield: 90%).

(2) Synthesis of Intermediate (1-2)

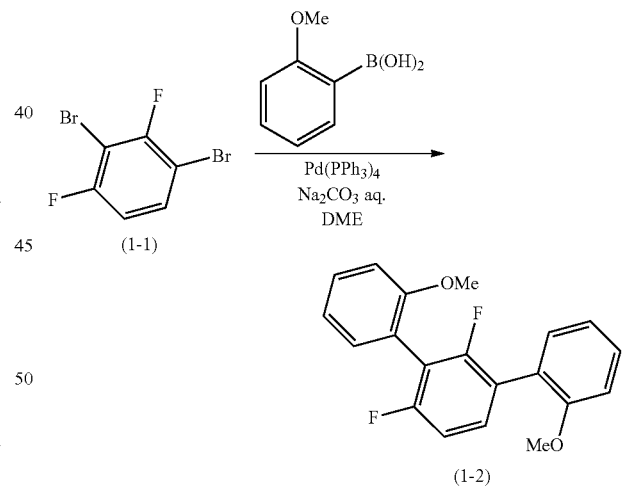

In an atmosphere of argon, 89.1 g (328 mmol) of intermediate (1-1), 109.6 g (721 mmol) of 2-methoxyphenylboronic acid, 15.2 g (13.1 mmol) of tetrakis(triphenylphosphine)palladium [Pd(PPh$_3$)$_4$] and 990 ml of an aqueous 2MNa$_2$CO$_3$ solution were added to 1.3 L of 1,2-dimethoxyethane (DME). In an atmosphere of argon, the mixture was stirred for 36 hours under reflux with heating. After bringing the temperature back to room temperature, 1 L of ethyl acetate was added, and an organic phase was isolated. The solvent was distilled off under reduced pressure. The resulting residues were dissolved in toluene. By purifying with silica gel column chromatography (eluent: toluene), 98.8 g of intermediate (1-2) as an intended product was obtained (yield: 92%).

(3) Synthesis of Intermediate (1-3)

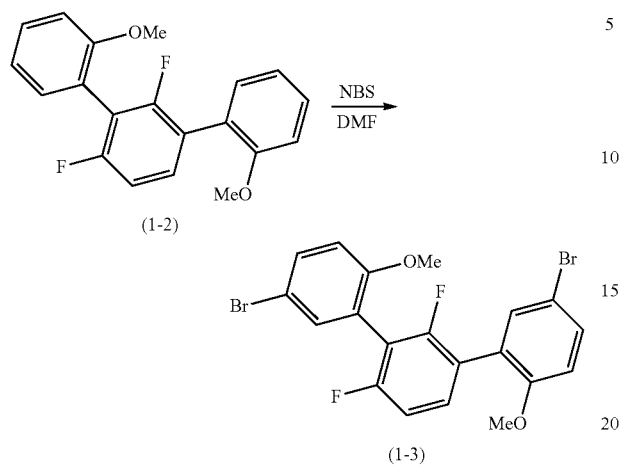

To a solution obtained by adding 98.8 g (303 mmol) of intermediate (1-2) to 500 ml of N,N-dimethylformamide (DMF), 113.2 g (636 mmol) of N-bromosuccinimide (NBS) that had been dissolved in 300 ml of DMF was added dropwise over 1 hour. After stirring for 1 hour at room temperature, an aqueous solution of sodium sulfite was added to the reaction liquid, and deposited solids were collected by filtration. These solids were washed with methanol and water in this sequence, and then dissolved in heated toluene. While keeping warm, this solution was purified by silica gel column chromatography (eluent: toluene), and was further washed by suspending in heptane, whereby 136.2 g (yield: 92%) of intermediate (1-3) as an intended product was obtained.

(4) Synthesis of Intermediate (1-4)

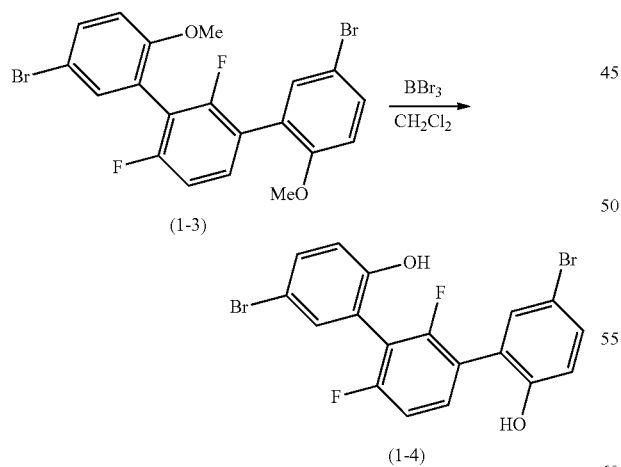

In an atmosphere of argon, a reaction solution obtained by adding 70.3 g (145 mmol) of intermediate (1-3) to 400 ml of dichloromethane was stirred at 0° C. Subsequently, a dichloromethane solution of 80.0 g (319 mmol) of boron tribromide was added dropwise. After bringing the temperature back to room temperature, stirring was conducted for 18 hours. Again, the temperature was lowered to 0° C., and 300 ml of water was added and an organic phase was isolated. The solvent was distilled off under reduced pressure. By purifying the resulting residues by silica gel column chromatography (eluent: toluene), 66.0 g of intermediate (1-4) as an intended product was obtained (yield: 99%).

(5) Synthesis of Intermediate (1-5)

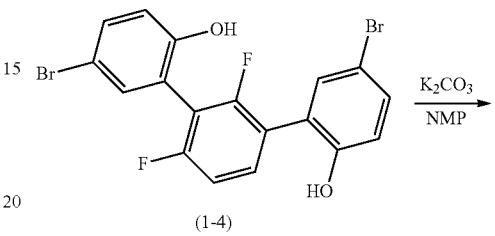

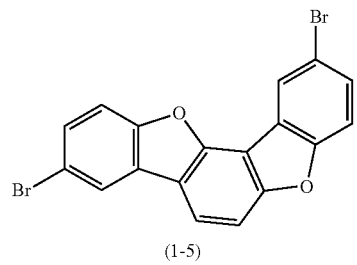

In an argon atmosphere, 10.0 g (21.9 mmol) of intermediate (1-4) and 12.0 g (87.7 mmol) of potassium carbonate were added to 100 ml of N-methyl-pyrrolidone (NMP), and the resultant was stirred at 180° C. for 15 hours. After bringing the temperature back to room temperature, 100 ml of water was added, and deposited solids were collected by filtration. The solids were dissolved in xylene by heating, and 10 g of silica gel was added. Then, filtration was conducted. The filtrate was concentrated, and the deposited solids were purified by repeating recrystallization from a xylene solvent, whereby 4.1 g of intermediate (1-5) as an intended product was obtained (yield: 45%).

(6) Synthesis of Compound A

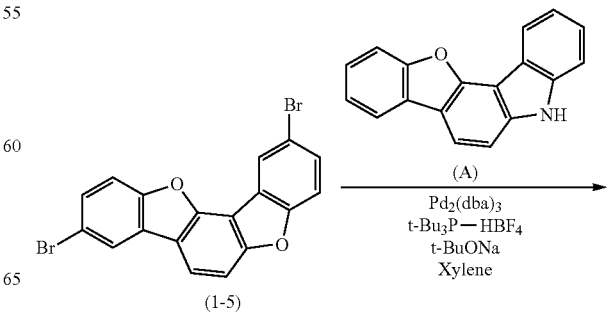

-continued

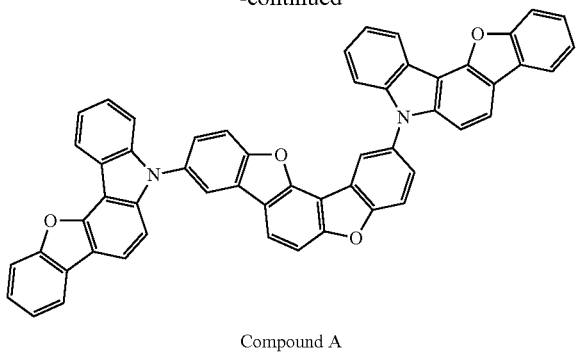

Compound A

In an argon atmosphere, 2.5 g (6.01 mmol) of intermediate (1-5), 3.9 g (15.0 mmol) of intermediate (A) synthesized in accordance with the method described in WO2009-148015, 0.22 g (0.24 mmol) of tris(dibenzylideneacetone)dipalladium(0) [$Pd_2(dba)_3$], 0.28 g (0.96 mmol) of tri-tert-butylphosphonium tetrafluoroborate [$t\text{-}Bu_3P\text{—}HBF_4$] and 1.6 g (16.6 mmol) of sodium t-butoxide were added to 50 ml of xylene, and the mixture was stirred at 150° C. for 24 hours. 800 ml of toluene was added and dissolved therein by heating. The resultant was purified by silica gel column chromatography (eluent: toluene). The solvent was distilled off under reduced pressure, and deposited solids were repeatedly washed with acetone, whereby 3.9 g (yield: 84%) of compound A was obtained as white solids.

As a result of a FD-MS analysis, the compound A had an m/e value of 768 relative to a molecular weight of 768.

Example 2

Compound B was synthesized by the following method.

(1) Synthesis of Intermediate (2-1)

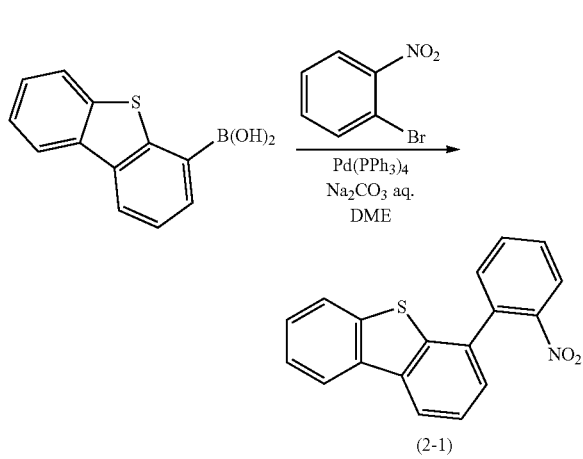

(2-1)

12.9 g (56.6 mmol) of dibenzothiophene-4-boronic acid, 12.6 g (62.2 mmol) of 2-nitrobromobenzene, 1.3 g (1.13 mmol) of $Pd(PPh_3)_4$ and 85 ml of an aqueous $2MNa_2CO_3$ solution were added to 260 ml of 1,2-dimethoxyethane (DME). In an argon atmosphere, the resulting mixture was stirred under reflux with heating for 24 hours. After bringing the temperature back to room temperature, 500 ml of toluene was added, and an organic phase was isolated. The solvent was distilled off under reduced pressure. The resulting residues were dissolved in toluene. By purifying by silica gel column chromatography (eluent: toluene), and by repeating recrystallization from a toluene solvent, 13.7 g of intermediate (2-1) as an intended product was obtained (yield: 80%).

(2) Synthesis of Intermediate (2-2)

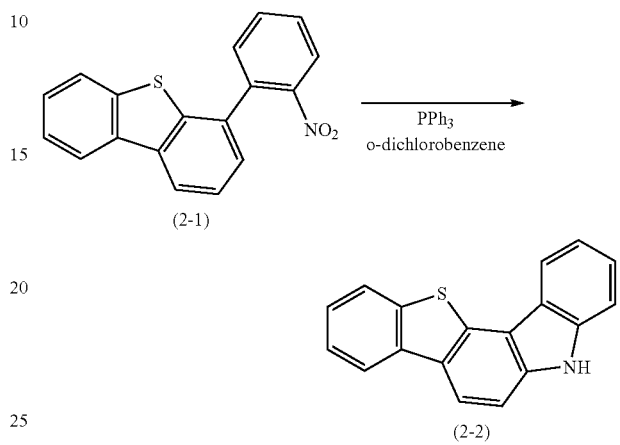

13.7 g (44.9 mmol) of intermediate (2-1) and 29.4 g (112 mmol) of triphenylphosphine were added to 200 ml of o-dichlorobenzene, and the resultant was stirred at 185° C. for 20 hours. The solvent was distilled off under reduced pressure. Methanol was added and deposited solids were collected by filtration. Toluene was added and the resulting mixture was washed by suspending in the toluene with heating, whereby 5.5 g of intermediate (2-2) as an intended product was obtained (yield: 45%).

(3) Synthesis of Compound B

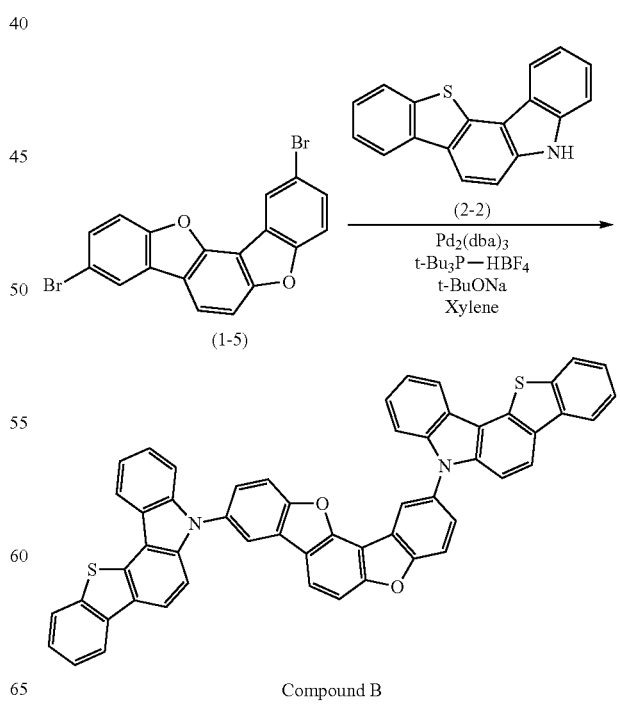

Compound B

Compound B was synthesized in the same manner as in Synthesis Example 1(6), except that intermediate (2-2) was used instead of intermediate (A).

As a result of a FD-MS analysis, compound B had an m/e value of 800 relative to a molecular weight of 800.

Fabrication and Evaluation of Organic EL Device

Example 3

A glass substrate of 25 mm by 75 mm by 1.1 mm thick with an ITO transparent electrode (manufactured by GEO-MATEC Co., Ltd.) was subjected to ultrasonic cleaning with isopropyl alcohol for 5 minutes, and then subjected to UV (Ultraviolet)-ozone cleaning for 30 minutes.

The cleaned glass substrate with the ITO transparent electrode lines was mounted in a substrate holder of a vacuum vapor deposition apparatus. On the surface where the ITO electrode lines were formed, the following compound (HI1) was deposited by resistance heating in a thickness of 20 nm so as to cover the ITO electrode lines. Subsequently, the following compound (HT1) was deposited by resistance heating in a thickness of 60 nm. As a result, thin films were formed in sequence. The film-forming rate was 1 Å/s. These thin films functions as a hole-injecting layer and a hole-transporting layer, respectively.

Subsequently, on the hole-transporting layer, as a host material, compound A produced in Example 1 and compound (D1) as a phosphorescent emitting material were co-deposited by resistance heating, whereby a 40 nm-thick thin film was formed. At this time, deposition was conducted such that the mass ratio of compound (D1) became 20% relative to the total mass of compound A and compound (D1). This thin film functions as a phosphorescent emitting layer.

Subsequently, on this phosphorescent emitting layer, compound (HBL1) was deposited by resistance heating, whereby a 5 nm-thick thin film was formed. This thin film functions as a hole-blocking layer.

Then, on this barrier layer, the following compound (ET1) was deposited by resistance heating, whereby a 25 nm-thick thin film was formed. This film functions as an electron-injecting layer.

Subsequently, on this electron-injecting layer, a 1.0 nm-thick LiF film was deposited.

Then, on this LiF film, metal aluminum was deposited to form an 80 nm-thick metal cathode, whereby an organic EL device was produced.

The compounds used in fabrication of the organic EL device are shown below.

HI1

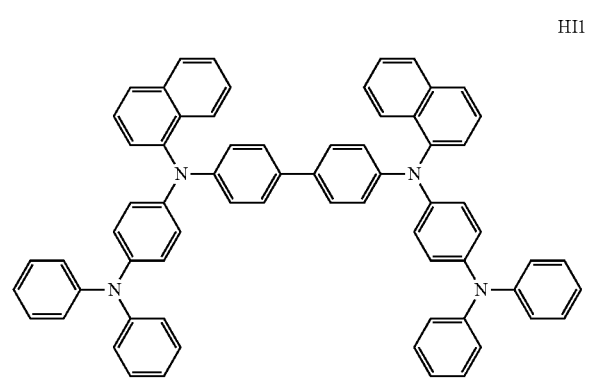

HT1

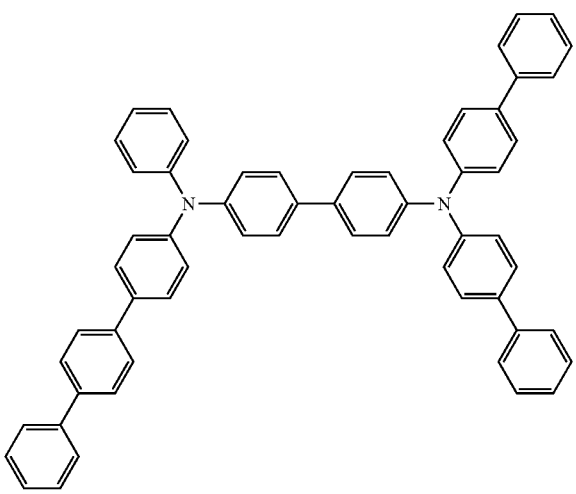

HBL1

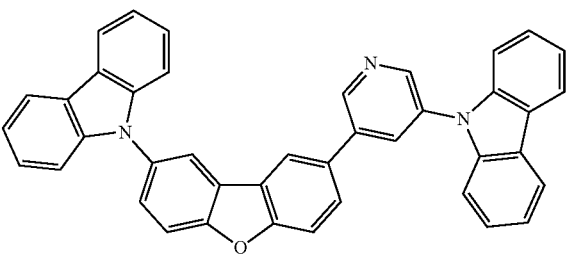

ET1

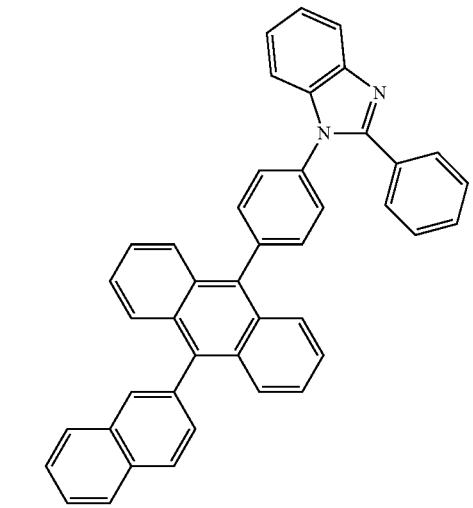

D1

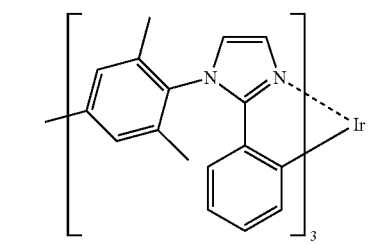

The organic EL device obtained above was allowed to emit light by DC driving, and luminance and current density were measured. A voltage and a luminous efficiency (external quantum efficiency) at a current density of 1 mA/cm$^2$

Example 4

An organic EL device was produced and evaluated in the same manner as in Example 3, except that compound B was used instead of compound A. The results are shown in Table 1.

Comparative Example 1

An organic EL device was produced and evaluated in the same manner as in Example 3, except that the following comparative compound 1 was used instead of compound A. The results are shown in Table 1.

Comp. Compound 1

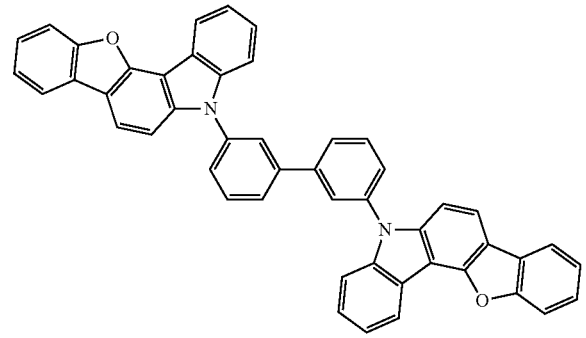

TABLE 1

|  | Host material | Voltage [V] | External quantum efficiency [%] |
|---|---|---|---|
| Example 3 | Compound A | 3.7 | 17.8 |
| Example 4 | Compound B | 3.6 | 17.5 |
| Comp. Ex. 1 | Comp. compound 1 | 4.2 | 14.6 |

Example 5

An organic EL device was fabricated in the same manner as in Example 3, except that a phosphorescent emitting layer was formed by using, as a host material, compound (H1) instead of compound A, and that a hole-barrier layer was formed by using compound A instead of compound (HBL1).

H1

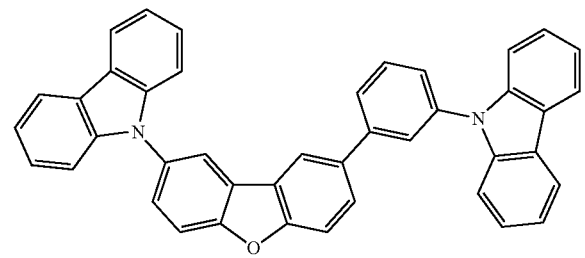

The organic EL device obtained above was allowed to emit light by DC driving, and luminance and current density were measured. A voltage and a luminous efficiency (external quantum efficiency) at a current density of 1 mA/cm² were obtained. Further, luminance 70% life time (referred to as "LT70"; the period for which luminance was reduced to 70%) at an initial luminance of 3000 cd/m² was obtained. The results of evaluation of these luminous characteristics are shown in Table 2.

Example 6

An organic EL device was produced and evaluated in the same manner as in Example 5, except that the hole-barrier layer was formed by using compound B instead of compound A. The results are shown in Table 2.

Comparative Example 2

An organic EL device was produced and evaluated in the same manner as in Example 5, except that the hole-barrier layer was formed by using comparative compound 1 instead of compound A. The results are shown in Table 2.

TABLE 2

|  | Hole-barrier material | Voltage [V] | External quantum efficiency [%] | LT70 luminance life [h] |
|---|---|---|---|---|
| Example 5 | Compound A | 3.8 | 17.9 | 215 |
| Example 6 | Compound B | 3.5 | 18.1 | 198 |
| Comp. Ex. 2 | Comp. compound 1 | 4.3 | 14.5 | 120 |

The triplet energy of the compounds used in the Examples was measured by the following method. The results are shown in Table 3.

The triplet energy was measured by a commercially-available device (F-4500, manufactured by Hitachi Ltd.). Specifically, each compound was dissolved in an EPA solvent (diethylether:isopentane:ethanol=5:5:5 (volume ratio), each solvent is spectrally graded) to obtain a sample (sample 10 µmol/l) for measuring phosphorescent emission. The sample for measuring phosphorescent emission put in a quarts cell was cooled to 77(K), and then irradiated with excited light. The phosphorescent intensity was measured while changing the wavelength.

The conversion formula of triplet energy ($E^T$) is as follows.

$$E^T \text{ (eV)} = 1239.85/\lambda_{ph}$$

The "$\lambda_{ph}$" (unit: nm) is defined as follows. When the phosphorescent intensity and the wavelength are taken at the vertical axis and the horizontal axis respectively to express a phosphorescent spectrum and a tangential line is drawn against the rise on the shorter wavelength side of the phosphorescent spectrum, a wavelength value of the intersection of the tangential line and the horizontal axis.

TABLE 3

| Name of Compound | Triplet energy [eV] |
|---|---|
| Compound A | 2.99 |
| Compound B | 2.95 |
| Comp. compound 1 | 2.95 |

The glass transition temperature (Tg, ° C.) of the compounds used in the Examples was measured. The results are shown in Table 4.

The glass transition temperature of the compound was measured by a commercially-available differential scanning calorimeter (PYRIS Diamond DSC, manufactured by PerkinElmer Japan Co., Ltd.). From a specific heat change curve obtained when heating is conducted at a temperature-elevating rate of 10° C./min in the flow of nitrogen, a point when the specific heat changed was obtained as a glass transition temperature.

TABLE 4

| Name of Compound | Glass transition temperature [° C.] |
| --- | --- |
| Compound A | 219 |
| Compound B | 234 |
| Comp. compound 1 | 150 |

From the results shown in Tables 1 to 3, it can be thought that the compound of the invention has a structure in which highly planar polycyclic hetero-aromatic rings are directly connected while keeping a high triplet energy, and hence, it is capable of fabricating a low-voltage driving and highly efficient organic EL device. Further, from the results shown in Table 4, it is apparent that the compound of the invention is a compound having a high glass transition temperature and excellent thermal stability, and hence it is suitable for use in fabrication of an organic EL device to which thermal load is applied.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The specification of a Japanese application on the basis of which the present application claims Paris Convention priority is incorporated herein by reference in its entirety.

The invention claimed is:

1. A compound that comprises three or more structures represented by the following formula (1) in the same molecule, where, in formula (1), $Z_1$, $Z_2$, $Z_3$, Xa, Xb and Xc make up a fused ring system, and in which at least three of the structures represented by the formula (1) are directly bonded to each other by a single bond between adjacent fused ring systems:

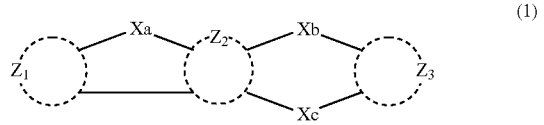

(1)

wherein in the formula (1),
Xa is O, S, N(R) or C(R1a)(R1b);
Xb and Xc are independently O, S, N(R), C(R1a)(R1b) or a single bond, provided that at least one of Xb and Xc is a single bond;
R is a single bond, a hydrogen atom, a substituted or unsubstituted alkyl group including 1 to 30 carbon atoms, a substituted or unsubstituted cycloalkyl group including 3 to 30 ring carbon atoms, a substituted or unsubstituted aromatic hydrocarbon ring group including 6 to 30 ring carbon atoms or a substituted or unsubstituted aromatic heterocyclic group including 3 to 30 ring atoms;
R1a and R1b are independently a hydrogen atom, a substituted or unsubstituted alkyl group including 1 to 30 carbon atoms, a substituted or unsubstituted cycloalkyl group including 3 to 30 ring carbon atoms, a substituted or unsubstituted aromatic hydrocarbon ring group including 6 to 30 ring carbon atoms or a substituted or unsubstituted aromatic heterocyclic group including 3 to 30 ring atoms;
provided that there is no case that both of Xa and Xb, or both of Xa and Xc are C(R1a)(R1b), and there is no case that both of Xa and Xb, or both of Xa and Xc are N(R);
$Z_1$, $Z_2$ and $Z_3$ are independently a substituted or unsubstituted aromatic hydrocarbon ring group including 6 to 30 ring carbon atoms or a substituted or unsubstituted aromatic heterocyclic group including 3 to 30 ring atoms;
provided that the three or more structures represented by the formula (1) may be the same as or different from each other;
provided that the compound does not contain a triphenylenyl group, and
wherein a number of single bond between adjacent fused ring systems of in formula (1) is one less than the number of structures represented formula (1) in the molecule.

2. The compound according to claim 1 that is represented by any of the following formulas (1a) to (1e):

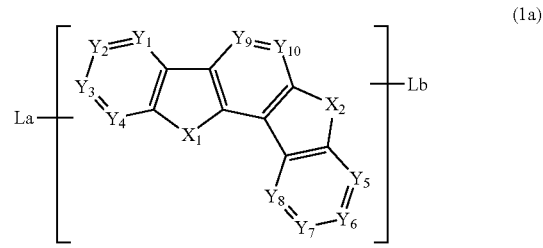

(1a)

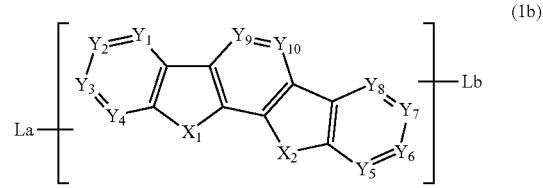

(1b)

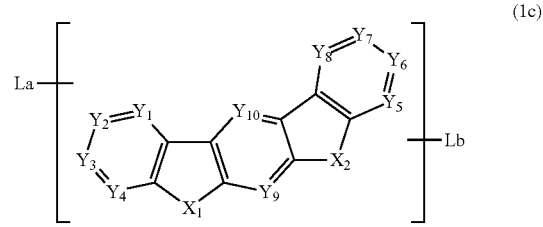

(1c)

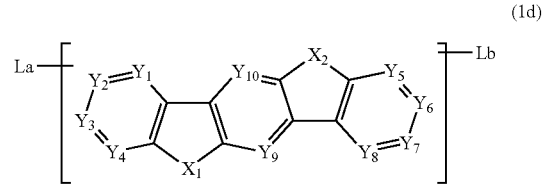

(1d)

(1e)

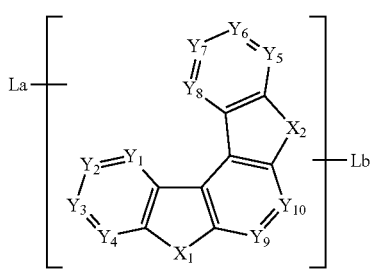

wherein in the formulas (1a), (1b), (1c), (1d) and (1e),
La and Lb are independently any of the structures represented by the following formulas (a) to (e);
$X_1$ and $X_2$ are independently O, S, N(R) or C(R1a)(R1b);
$Y_1$ to $Y_{10}$ are independently C(R1) or a nitrogen atom;
R and R1 are independently a single bond, a hydrogen atom, a substituted or unsubstituted alkyl group including 1 to 30 carbon atoms, a substituted or unsubstituted cycloalkyl group including 3 to 30 ring carbon atoms, a substituted or unsubstituted aromatic hydrocarbon ring group including 6 to 30 ring carbon atoms or a substituted or unsubstituted aromatic heterocyclic group including 3 to 30 ring atoms;
R1s that bond to adjacent carbon atoms may be bonded to each other to form a ring;
R1a and R1b are independently a hydrogen atom, a substituted or unsubstituted alkyl group including 1 to 30 carbon atoms, a substituted or unsubstituted cycloalkyl group including 3 to 30 ring carbon atoms, a substituted or unsubstituted aromatic hydrocarbon ring group including 6 to 30 ring carbon atoms or a substituted or unsubstituted aromatic heterocyclic group including 3 to 30 ring atoms;
both of La and Lb independently bond to any of $X_1$ to $X_2$ and $Y_1$ to $Y_{10}$; or one of La and Lb bonds to any of $X_1$ to $X_2$ and $Y_1$ to $Y_{10}$ and the other of La and Lb bonds to Lc, and the Lc bonds to any of $X_1$ to $X_2$ and $Y_1$ to $Y_{10}$;
Lc is a substituted or unsubstituted aromatic hydrocarbon ring group including 6 to 30 ring carbon atoms or a substituted or unsubstituted aromatic heterocyclic group including 3 to 30 ring atoms;
provided that there is no case that both $X_1$ and $X_2$ are C(R1a)(R1b) and there is no case that both $X_1$ and $X_2$ are NR:

(a)

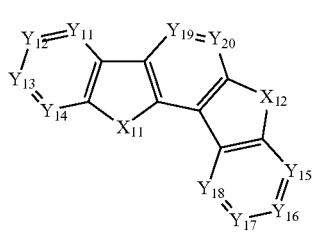

(b)

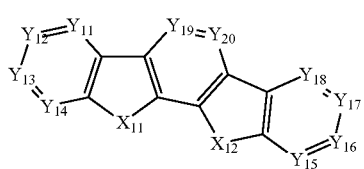

(c)

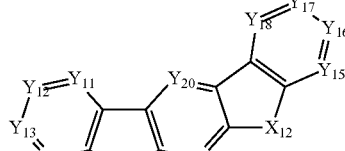

(d)

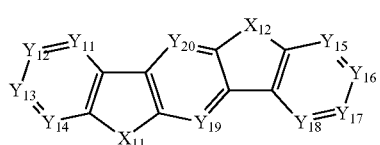

(e)

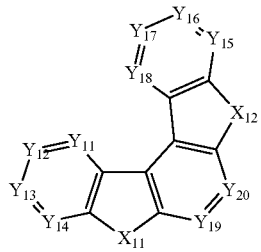

wherein in the formulas (a), (b), (c), (d) and (e),
$X_{11}$ and $X_{12}$ are independently the same as $X_1$ and $X_2$ in the formulas (1a) to (1e);
$Y_{11}$ to $Y_{20}$ are independently the same as $Y_1$ to $Y_{10}$ in the formulas (1a) to (1e); and
one of $X_{11}$ to $X_{12}$ and $Y_{11}$ to $Y_{20}$ bonds to the structure represented by the formulas (1a) to (1e).

3. The compound according to claim 2, wherein La and Lb independently bond to any of $X_1$ to $X_2$ and $Y_1$ to $Y_{10}$.

4. The compound according to claim 2, wherein one of $X_1$ and $X_2$ in the formulas (1a) to (1e) is N(R) and the other of $X_1$ and $X_2$ is an oxygen atom or a sulfur atom.

5. The compound according to claim 2, wherein $X_1$ and $X_2$ in the formulas (1a) to (1e) are independently an oxygen atom or a sulfur atom.

6. The compound according to claim 2, wherein at least one of La and Lb is represented by any of the following formulas (f) to (j):

(f)

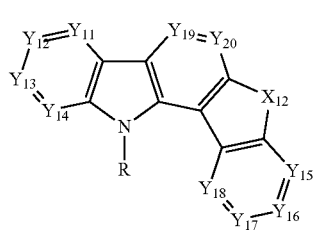

(g)

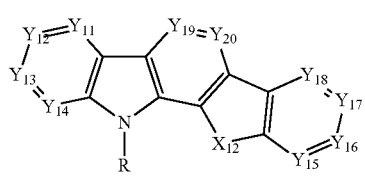

-continued (h)
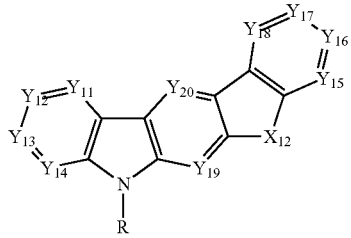

(i)
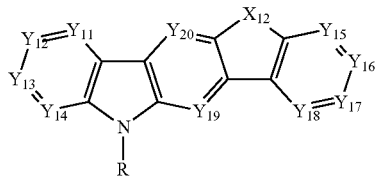

(j)
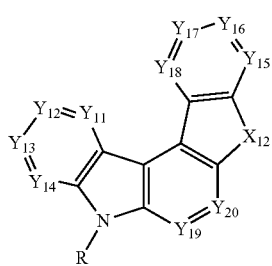

wherein in the formulas (f) to (j), $X_{12}$, R, $Y_{11}$ to $Y_{20}$ are the same as those in the formulas (1a) to (1e).

7. The compound according to claim 6 that is represented by the following formula (2):

(2)
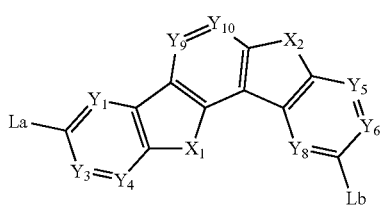

wherein in the formula (2), $X_1$, $X_2$, $Y_1$, $Y_3$ to $Y_6$, $Y_8$ to $Y_{10}$, La and Lb are the same as those in the formulas (1a) to (1e).

8. The compound according to claim 7, wherein in the formula (2), at least one of La and Lb is represented by any of the formulas (f) to (j).

9. The compound according to claim 7, wherein in the formula (2), La and Lb are independently represented by any of the formulas (f) to (j), and Rs in the formulas (f) to (j) are both single bonds, and bond to a carbon atom in a part indicated by * in the formula (2a):

(2a)
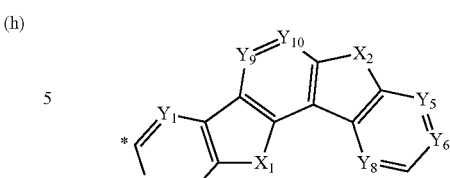

wherein in the formula (2a), $X_1$, $X_2$, $Y_1$, $Y_3$ to $Y_6$, and $Y_8$ to $Y_{10}$, are the same as those in the formula (2).

10. A material for an organic electroluminescence device that comprises the compound according to claim 1.

11. An organic electroluminescence device that comprises a cathode and an anode; one or more organic thin film layers including an emitting layer between the cathode and the anode; and at least one layer of the organic thin film layer(s) comprises the material for an organic electroluminescence device according to claim 10.

12. The organic electroluminescence device according to claim 11, wherein the emitting layer comprises the material for an organic electroluminescence device.

13. An organic electroluminescence device that comprises a cathode and an anode, and one or more organic thin film layers including an emitting layer between the cathode and the anode, wherein the organic thin film layers comprise one or more emitting layers, and at least one layer of the emitting layer(s) comprises the material for an organic electroluminescence device and an phosphorescent emitting material, said material for an organic electroluminescence material comprises a compound according to claim 1.

14. The organic electroluminescence device according to claim 13, wherein the phosphorescent emitting material comprises a metal complex compound, and the metal complex compound comprises a metal atom selected from the group consisting of Ir, Pt, Os, Au, Cu, Re and Ru, and a ligand.

15. An organic electroluminescence device that comprises a hole-transporting zone between an emitting layer and an anode, wherein the hole-transporting zone has one or more organic thin film layers, and at least one layer of the organic thin film layer(s) comprises the material for an organic electroluminescence device according to claim 10.

16. The organic electroluminescence device according to claim 15, wherein, in the hole-transporting zone, an organic thin film layer that contacts the emitting layer comprises the material for an organic electroluminescence device.

17. An organic electroluminescence device that comprises an electron-transporting zone between an emitting layer and a cathode, wherein the electron-transporting zone has one or more organic thin film layers, and at least one layer of the organic thin film layer(s) comprises the material for an organic electroluminescence device according to claim 10.

18. The organic electroluminescence device according to claim 17, wherein, in the electron-transporting zone, an organic thin film layer that contacts the emitting layer comprises the material for an organic electroluminescence device.

19. The compound according to claim 2 that is represented by the following formula (2):

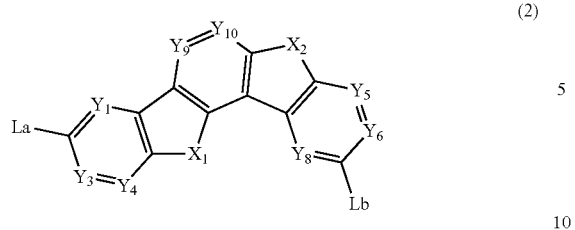
wherein in the formula (2), $X_1$, $X_2$, $Y_1$, $Y_3$ to $Y_6$, $Y_8$ to $Y_{10}$, La and Lb are the same as those in the formulas (1a) to (1e).
* * * * *